US008748382B2

(12) United States Patent
Dey et al.

(10) Patent No.: US 8,748,382 B2
(45) Date of Patent: *Jun. 10, 2014

(54) METHOD OF DRUG DELIVERY FOR BONE ANABOLIC PROTEIN

(75) Inventors: Michael J. Dey, Sandbach (GB); Nathalie Mondoly, Le Chesnay (FR); Benedicte Rigaud, Oulins (FR); Bart Henderson, Belmont, MA (US); C. Richard Lyttle, Bala Cynwyd, PA (US)

(73) Assignees: Radius Health, Inc., Cambridge, MA (US); Ipsen Pharma S.A.S., Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,086

(22) Filed: Apr. 3, 2012

(65) Prior Publication Data

US 2013/0157955 A1 Jun. 20, 2013

Related U.S. Application Data

(63) Continuation of application No. 12/855,458, filed on Aug. 12, 2010, now abandoned, which is a continuation of application No. 12/151,975, filed on May 9, 2008, now Pat. No. 7,803,770, which is a continuation-in-part of application No. PCT/US2007/021216, filed on Oct. 3, 2007.

(60) Provisional application No. 60/848,960, filed on Oct. 3, 2006.

(51) Int. Cl.
*A61K 38/00* (2006.01)
*A61K 38/29* (2006.01)

(52) U.S. Cl.
USPC .......... 514/16.7; 514/9.7; 514/11.8; 514/16.9

(58) Field of Classification Search
None
See application file for complete search history.

(56) References Cited

U.S. PATENT DOCUMENTS

| | | |
|---|---|---|
| 5,589,452 A | 12/1996 | Krstenansky et al. |
| 5,693,616 A | 12/1997 | Krstenansky et al. |
| 5,695,955 A | 12/1997 | Krstenansky et al. |
| 5,723,577 A | 3/1998 | Dong |
| 5,798,225 A | 8/1998 | Krstenansky et al. |
| 5,807,823 A | 9/1998 | Krstenansky et al. |
| 5,821,225 A | 10/1998 | Vickery |
| 5,840,837 A | 11/1998 | Krstenansky et al. |
| 5,874,086 A | 2/1999 | Krstenansky et al. |
| 5,955,574 A | 9/1999 | Dong |
| 5,969,095 A | 10/1999 | Dong |
| 5,977,070 A | 11/1999 | Piazza et al. |
| 6,051,686 A | 4/2000 | Krstenansky et al. |
| 6,136,784 A | 10/2000 | L'Italien et al. |
| 6,544,949 B1 | 4/2003 | Dong |
| 6,583,114 B2 | 6/2003 | Vickery |
| 6,756,480 B2 | 6/2004 | Kostenuik et al. |
| 6,770,623 B1 | 8/2004 | Chang et al. |
| 6,849,710 B1 | 2/2005 | Arzeno |
| 6,921,750 B2 | 7/2005 | Dong |
| 7,371,721 B2 | 5/2008 | Henriksen et al. |
| 7,410,948 B2 | 8/2008 | Dong |
| 7,803,770 B2 | 9/2010 | Dey et al. |
| 8,148,333 B2 | 4/2012 | Dey et al. |
| 2002/0077281 A1 | 6/2002 | Vickery |
| 2003/0039654 A1 | 2/2003 | Kostenuik et al. |
| 2003/0166836 A1 | 9/2003 | Dong |
| 2004/0214996 A1 | 10/2004 | Kostenuik et al. |
| 2005/0124537 A1 | 6/2005 | Kostenuik et al. |
| 2005/0282749 A1 | 12/2005 | Henriksen et al. |
| 2007/0299009 A1 | 12/2007 | Dong |
| 2008/0119401 A1 | 5/2008 | Dong |
| 2010/0029556 A1 | 2/2010 | Dey et al. |
| 2011/0092425 A1 | 4/2011 | Dey et al. |

FOREIGN PATENT DOCUMENTS

| | | |
|---|---|---|
| CA | 2555848 A1 | 8/2005 |
| CN | 1281370 A | 1/2001 |
| EP | 0 822 200 A1 | 2/1998 |
| EP | 1 417 972 A1 | 5/2004 |
| EP | 0 822 200 B1 | 9/2004 |
| JP | 7-509228 | 10/1995 |
| JP | 2002-512973 | 5/2002 |
| WO | WO 94/01460 | 1/1994 |
| WO | WO 96/40775 | 12/1996 |
| WO | WO 97/02834 | 1/1997 |
| WO | WO 97/07815 | 3/1997 |
| WO | WO 98/30590 | 7/1998 |
| WO | WO 99/12561 | 3/1999 |
| WO | WO 99/29337 A1 | 6/1999 |
| WO | WO 99/55353 | 11/1999 |

(Continued)

OTHER PUBLICATIONS

Bostrom, M.P.G. et al., "Parathyroid Hormone-Related Protein Analog RS-66271 is an Effective Therapy for Impaired Bone Healing in Rabbits on Corticosteroid Therapy," *Bone*, 26(5):437-442 (2000).

Culler, M.D. et al., "BIM-44058, a Novel Analog of PTHrP with Enhanced Bone Building Activity, but Decreased Calcium-Mobilization Potential," Twenty-Third Annual Meeting of the American Society of Bone and Mineral Research, Phoenix, Arizona, USA, Oct. 12-16, 2001, *J. Bone Miner. Res.*, (Abstract M460), 16(Suppl. 1):S540 (2001).

Culler, M.D. et al., "A Novel PTHRP Analog with Decreased Calcium-Mobilization Potential, but with Enhanced Bone Building Activity," S19, Abstract for the World Congress on Osteoporosis meeting held on May 10-14, 2002, Lisbon, Portugal (Abstract P51SU), *Osteoporos Int* 13(1) (Apr. 2002).

(Continued)

*Primary Examiner* — Elizabeth C Kemmerer
(74) *Attorney, Agent, or Firm* — Hamilton, Brook, Smith & Reynolds, P.C.

(57) ABSTRACT

The present invention provides a storage-stable composition containing a parathyroid hormone-related protein (PTHrP) and methods of using a PTHrP and the PTHrP compositions described herein to treat osteoporosis, to increase bone mass or to increase bone quality. The composition is storage stable, in sterile form, and in general may be stored at room temperature for at least several weeks to allow convenient parenteral administration to human patients.

12 Claims, 6 Drawing Sheets

(56) References Cited

FOREIGN PATENT DOCUMENTS

| WO | WO 01/81415 A2 | 11/2001 |
|----|----|----|
| WO | WO 03/105772 A2 | 12/2003 |
| WO | WO 2004/060386 A1 | 7/2004 |
| WO | WO 2005/115441 A2 | 12/2005 |
| WO | WO 2008/063279 A2 | 5/2008 |
| WO | WO 2009/137093 A1 | 11/2009 |

OTHER PUBLICATIONS

Dempster, D.W. et al., "Anabolic Actions of Parathyroid Hormone on Bone," *Endocr Rev*, 14(6):690-709 (1993).

Dempster, D.W. et al., "Effects of Daily Treatment with Parathyroid Hormone on Bone Microarchitecture and Turnover in Patients with Osteoporosis: A Paired Biopsy Study," *J. Bone Miner Res.*, 16:1846-1853 (2001).

Dong, J.Z. et al., "Development of Highly Potent Human Parathyroid Hormone Analogs," *Peptides: Biology and Chemistry, Proceedings of the Chinese Peptide Symposium, 4th*, Chengdu, Peop. Rep. China, Jul. 21-25, 1996, pp. 173-175 (1998).

Dong, J.Z. et al., "Highly Potent Analogs of Human Parathyroid Hormone and Human Parathyroid Hormone-Related Protein," *Peptides: The Wave of the Future, Proceedings of the Second International and the Seventeenth American Peptide Symposium*, San Diego, CA USA, Jun. 9-14, 2001, pp. 668-669 (2001).

Dong, J.Z. et al., "Highly Potent Human Parathyroid Hormone Analogs," *Peptides: Frontiers of Peptide Science, Proceedings of the American Peptide Symposium, 15th*, Nashville, Jun. 14-19, 1997, pp. 541-542 (1999).

Everhart-Caye, M. et al., "Parathyroid Hormone (PTH)-Related Protein(1-36) is Equipotent to PTH(1-34) in Humans," *J Clin Endocrinol Metab*, 81(1):199-208 (1996).

Fraher, L.J. et al., "A Comparison of the in Vivo Biochemical Responses to Exogenous Parathyroid Hormone-(1-34) [PTH-(1-34)] and PTH-Related Peptide-(1-34) in Man," *J Clin Endocrinol Metab*, 75(2):417-423 (1992).

Fraher, L.J. et al., "Comparison of the Pharmacokinetics of Parenteral Parathyroid Homone-(1-34) [PTH-(1-34)] and PTH-Related Peptide-(1-34) in Healthy Young Humans," *J Clin Endocrinol Metab*, 80(1):60-64 (1995).

Frolik, C.A. et al., "Comparison of Recombinant Human PTH(1-34) (LY333334) with a C-Terminally Substituted Analog of Human PTH-Related Protein (1-34) (RS-66271): In Vitro Activity and In Vivo Pharmacological Effects in Rats," *J. Bone Miner. Res.*, 14(2):163-172 (1999).

Frolik, C.A. et al., "Reply: Further Data are Required to Assure that the Discrepant Binding Affinity is Explained by Different Receptor Conformations," *J. Bone Miner Res.*, 15(3):608 (2000).

Henry, J.G. et al., "Parathyroid Hormone-Related Protein-(1-36) is Biologically Active When Administered Subcutaneously to Humans," *J Clin Endocrinol Metab*, 82(3):900-906 (1997).

Hildebrand, T. et al., "Direct Three-Dimensional Morphometric Analysis of Human Cancellous Bone: Microstructural Data from Spine, Femur, Iliac Crest, and Calcaneus," *J. Bone Miner Res*, 14(7):1167-1174 (1999).

Hoare, S.R.J. and Usdin, T.B., "Letter to the Editor: The Discrepancy Between the Binding Affinity of PTH (1-34) and RS 66271 is Explained by Interaction of the PTH/PTHrP Receptor with G-Protein," *J. Bone Miner. Res.*, 15(3):605-607 (2000).

Hoare, S.R.J. and Usdin, T.B., "Quantitative Cell Membrane-Based Radioligand Binding Assays for Parathyroid Hormone Receptors," *J. Pharmacol. Toxicol.*, 41:83-90 (1999).

Horwitz, M.J. et al., "Continuous PTH and PTHrP Infusion Causes Suppression of Bone Formation and Discordant Effects on 1,25(OH)$_2$ Vitamin D," *J Bone Miner Res*, 20(10):1792-1803 (2005).

Horwitz, M.J. et al., "Direct Comparison of Sustained Infusion of Human Parathyroid Hormone-Related Protein-(1-36) [hPTHrP-(1-36)] Versus hPTH-(1-34) on Serum Calcium, Plasma 1,25-Dihydroxyvitamin D Concentrations, and Fractional Calcium Excretion in Healthy Human Volunteers," *J Clin Endocrinol Metab*, 88(4):1603-1609 (2003).

Horwitz, M.J. et al., "Safety and Tolerability of Subcutaneous PTHrP(1-36) in Healthy Human Volunteers: a Dose Escalation Study," *Osteoporos Int*, 17:225-230 (2006).

Horwitz, M.J. et al., "Short-Term, High-Dose Parathyroid Hormone-Related Protein as a Skeletal Anabolic Agent for the Treatment of Postmenopausal Osteoporosis," *J Clin Endocrinol Metab*, 88(2):569-575 (2003).

Krstenansky, J.L. et al., "RS-66271: Molecular Design and in vivo Bone Anabolic Activity," Peptides 1994, Proceedings of the European Peptide Symposium, 23$^{rd}$, Braga, Port., Sep. 4-10, 1994:133-134 (1995).

Legrand, J. et al., "BIM-44058, a Novel PTHrP Analog, Does Not Increase Total Plasma Calcium in Cynomolgus Monkeys at an Effective Pharmacological Dose," Twenty-Third Annual Meeting of the American Society of Bone and Mineral Research, Phoenix, Arizona, USA, Oct. 12-16, 2001, *J Bone Miner Res* (Abstract M454) 16 (Suppl. 1):S539 (2001).

Legrand, J. et al., "BIM-44058, a Novel PTHrP Analog, Increases Bone Formation But Not Bone Resorption Histomorphometric Parameters in Old Ovariectomized Osteopenic Cynomolgus Monkeys," Twenty-Third Annual Meeting of the American Society of Bone and Mineral Research, Phoenix, Arizona, USA, Oct. 12-16, 2001, *J Bone Miner Res* (Abstract M455) 16 (Suppl. 1):S539 (2001).

Legrand, J. et al., "BIM-44058, a Novel PTHrP Analog, Restores in Vivo Spinal Bone Mineral Density in Old Ovariectomized Osteopenic Cynomolgus Monkeys," Twenty-Third Annual Meeting of the American Society of Bone and Mineral Research, Phoenix, Arizona, USA, Oct. 12-16, 2001, *J Bone Miner Res* (Abstract M453) 16 (Suppl. 1):S539 (2001).

Legrand, J-J. et al., "BIM-44058, A Novel PTHrP Analog, Restores BMD by Selectively Increasing Bone Formation in Old Ovariectomized, Osteopenic Cynomolgus Monkeys," S20, Abstract for the World Congress on Osteoporosis meeting held on May 10-14, 2002, Lisbon, Portugal (Abstract P53SA), *Osteoporos Int* 13(1) (Apr. 2002).

Mannstadt, M. et al., "Receptors for PTH and PTHrP: Their Biological Importance and Functional Properties," *American Physiological Society: Invited Review*:F665-F675 (1999).

Martin, T.J., "Osteoblast-derived PTHrP is a Physiological Regulator of Bone Formation," *J Clin Invest*, 115(9):2322-2324 (2005).

Miao, D. et al., "Osteoblast-derived PTHrP is a Potent Endogenous Bone Anabolic Agent that Modifies the Therapeutic Efficacy of Administered PTH 1-34," *J Clin Invest*, 115(9):2402-2411 (2005).

Murrills, R.J. et al., "In vitro and in vivo Activities of C-Terminally Tuncated PTH Peptides Reveal a Disconnect Between cAMP Signaling and Functional Activity," *Bone*, 35:1263-1272 (2004).

Neer, R.M. et al., "Effect of Parathyroid Hormone (1-34) on Fractures and Bone Mineral Density in Postmenopausal Women with Osteoporosis," *N. Engl. J. Med.*, 344(19):1434-1441 (2001).

O'Dea, L.S., et al., "BA058, a Novel Analog of Human Parathyroid Hormone-Related Peptide (PTHrP), Induces Evidence of Bone Formation without Evidence of Bone Resorption over 7 Days of Exposure," *The Endocrine Society's 89$^{th}$ Annual Meeting* held on Jun. 2-5, 2007, (Abstract) P2-137:361 (published on May 11, 2007).

Odgaard, A. And Gundersen, H.J.G., "Quantification of Connectivity in Cancellous Bone, with Special Emphasis on 3-D Reconstructions," *Bone*, 14:173-182 (1993).

Odgaard, A., "Three-Dimensional Methods for Quantification of Cancellous Bone Arhitecture," *Bone*, 20(4):315-328 (1997).

Pellegrini, M. et al., "Addressing the Tertiary Structure of Human Parathyroid Hormone-(1-34)," *J. Biol. Chem.*, 273(17):10420-10427 (1998).

Pellegrini, M. et al., "RS-66271, a Clinical Candidate Derived from Parathyroid Hormone Related Protein: the Role of Enhanced Amphiphilic Helicity," Peptipes: Frontiers of Peptide Science, Proceedings of the American Peptide Symposium, 15th, Nashville, Jun. 14-19, 1997 (1999), 392-393.

Pellegrini, M. et al., "Conformational Studies of RS-66271, an Analog of Parathyroid Hormone-Related Protein with Pronounced Bone Anabolic Activity," *J. Med. Chem.*, 40(19):3025-3031 (1997).

Plotkin, H. et al., "Dissociation of Bone Formation from Resorption during 2-Week Treatment with Human Parathyroid Hormone-Re-

(56) References Cited

OTHER PUBLICATIONS lated Peptide-(1-36) in Humans: Potential as an Anabolic Therapy for Osteoporosis," *J Clin Endocrinol Metab*, 83(8):2786-2791 (1998).
Toniolo, C., "$C^{\alpha,\alpha}$—Symmetrically Disubstituted Glycines: Useful Building Blocks in the Design of Conformationally Restricted Peptides", *Janssen Chim. Acta*, 11:10-16 (1993).
Vickery, B.H. et al., "RS-66271, a C-Terminally Substituted Analog of Human Parathyroid Hormone-Related Protein (1-34), Increases Trabecular and Cortical Bone in Ovariectomized, Osteopenic Rats," *J. Bone Miner. Res.*, 11(12):1943-1951 (1996).
Notification Concerning Transmittal of International Preliminary Report on Patentability, and International Preliminary Report on Patentability, International Application No. PCT/US2007/021216, Date of Mailing Jun. 4, 2009.
Notification of Transmittal of the International Search Report and the Written Opinion of the International Searching Authority, or the Declaration, International Search Report, and Written Opinion of the International Searching Authority, International Application No. PCT/US2007/021216, Date of Mailing Sep. 25, 2008.
Notification of Transmittal of the International Search Report and the Written Opinion of the International Searching Authority, or the Declaration, International Search Report, and Written Opinion of the International Searching Authority, International Application No. PCT/US2009/002868, Date of Mailing Aug. 3, 2009.
Bellido, T. et al., "Estrogen Inhibit Apoptosis of Osteoblasts and Osteocytes through Rapid (Non-genomic) Activation of Extracellular Signal-Regulated Kinases (ERKs)," *Journal of Bone and Mineral Research*, 14(Supp 1)(Abstract SA135):S342 (1999).
Bodenner, D.L. et al., "Essential Requirement of the Estrogen Receptor α or β for (Non-Genomic) Anti-Apoptotic Effects of Estrogen," *Journal of Bone and Mineral Research*, 14(Supp 1)(Abstract F071):S227 (1999).
Fox, J., "Developments in Parathyroid Hormone and Related Peptides as Bone-Formation Agents," *Current Opinion in Pharmacology*, 2:338-344 (2002).
Gallagher, J.C. et al., "PTHrP(1-34) Analog, Semparatide Acetate (RS-66271), Causes Sustained Increases in Spine in Postmanopausal Osteoporotic Women: Two Randomized Placebo-Controlled Trials," *Journal of Bone and Mineral Research*, 14(Supp 1)(Abstract 1018):S137 (1999).
Manolagas, S.C., "Activators of Non-Genomic Estrogen-Like Signalling (ANGELS): a Novel Class of Small Molecules with Bone Anabolic Properties," *Journal of Bone and Mineral Research*, 14(Supp 1)(Abstract 1191):S180 (1999).
Manolagas, S.C. et al., "Opposite Effects of Estrogen on the Life Span of Osteoblasts/Osteocytes Versus Osteoclasts In Vitro: An Explanation of the Imbalance between Formation and Resorption in Estrogen Deficiency," *Journal of Bone and Mineral Research*, 14(Supp 1)(Abstract 1147):S169 (1999).
Roe, E.B. et al., "Parathyroid Hormone 1-34 (hPTH 1-34) and Estrogen Produce Dramatic Bone Density Increases in Postmenopausal Osteoporosis—Results from a Placebo-Controlled Randomized Trial," *Journal of Bone and Mineral Research*, 14(Supp 1)(Abstract 1019):S137 (1999).
Notification Concerning Transmittal of International Preliminary Report on Patentability, International Application No. PCT/US2009/002868, Date of Mailing Nov. 18, 2010.
English Translation of Chinese Office Action dated Oct. 12, 2010, Chinese Patent Application No. 200780037021.9.
Office Action mailed Oct. 5, 2011, U.S. Appl. No. 12/855,458.
Notice of Abandonment mailed Apr. 23, 2012, U.S. Appl. No. 12/855,458.
Office Action, Mailed: Dec. 31, 2009, U.S. Appl. No. 12/151,975.
Final Office Action, Mailed: May 18, 2010, U.S. Appl. No. 12/151,975.
Notice of Allowance, Mailed: Jul. 23, 2010, U.S. Appl. No. 12/151,975.
Office Action, Mailed: Apr. 11, 2011, U.S. Appl. No. 12/311,418.
Notice of Allowance, Mailed: Dec. 14, 2011, U.S. Appl. No. 12/311,418.
Chantasingh, D., et al., "Cloning, Expression, and Characterization of a Xylanase 10 from *Aspergillus terreus* (BCC129) in *Pichia Pastoris*," Protein Expr. Purif., 46(1):143-149 (2006) (Abstract Only).
Legrand, J.J., et al., "Use of Biochemical Markers to Monitor Changes in Bone Turnover in Cynomolgus Monkeys," Biomarkers, 8(1): 63-77 (2003).

US 8,748,382 B2

METHOD OF DRUG DELIVERY FOR BONE ANABOLIC PROTEIN

RELATED APPLICATIONS

This application is a continuation of U.S. application Ser. No. 12/855,458, now abandoned, filed on Aug. 12, 2010, which is a continuation of U.S. application Ser. No. 12/151,975, filed on May 9, 2008, now U.S. Pat. No. 7,803,770 B2, issued Sep. 28, 2010, which is a continuation-in-part of International Application No. PCT/US2007/021216, which designated the United States and was filed on Oct. 3, 2007, published in English, which claims the benefit of U.S. Provisional Application No. 60/848,960, filed on Oct. 3, 2006. The entire teachings of the above applications are incorporated herein by reference.

BACKGROUND OF THE INVENTION

Parathyroid hormone-related protein ("PTHrP") is a 139 to 173 amino acid-protein. PTHrP and certain analogs are known to be useful to improve bone mass and quality in the treatment of osteoporosis and related disorders. However, the commercial use of these proteins as pharmaceutical agents requires the development of a formulation that is acceptable in terms of storage stability and ease of preparation.

Furthermore, currently available osteoporosis drugs have limitations on suitable dosage ranges due to the unwanted side-effects, such as hypercalcemia and increased stimulation of bone resorption. These unwanted side-effects and resulting dose limitations reduce the beneficial effects which can be achieved from these drugs. Thus a need exists for compounds which can be administered at a dose which will increase the beneficial effects without an increase in the unwanted side-effects.

SUMMARY OF THE INVENTION

The present invention provides a storage-stable composition containing a parathyroid hormone-related protein (PTHrP) and methods of using PTHrPs and the PTHrP compositions described herein to treat osteoporosis, to increase bone mass or to increase bone quality. The composition is storage stable, in sterile form, and in general may be stored at room temperature for at least several weeks to allow convenient parenteral administration to human patients.

In one embodiment, the present invention provides a storage-stable composition suitable for administration to a subject (e.g., a human). The composition comprises a PTHrP and an effective amount of buffer to maintain the pH of the composition between 2 and 7. In a particular embodiment, the PTHrP is [Glu$^{22,25}$, Leu$^{23,28,31}$, Aib$^{29}$, Lys$^{26,30}$]hPTHrP(1-34)NH$_2$ (SEQ ID NO.: 2).

In another embodiment, the present invention provides a sealed container containing a storage-stable composition suitable for administration to a subject. The composition comprises PTHrP or an analog thereof and an effective amount of buffer to maintain the pH of the composition between 2 and 7. In a particular embodiment, the PTHrP is [Glu$^{22,25}$, Leu$^{23,28,31}$, Aib$^{29}$, Lys$^{26,30}$]hPTHrP(1-34)NH$_2$ (SEQ ID NO.: 2).

In another embodiment, the present invention provides a drug delivery device comprising one or more than one single-use container which comprises a storage stable composition comprising PTHrP or an analog thereof and an effective amount of buffer to maintain the pH of the composition between 2 and 7. In a particular embodiment, the PTHrP is [Glu$^{22,25}$, Leu$^{23,28,31}$, Aib$^{29}$, Lys$^{26,30}$]hPTHrP(1-34)NH$_2$ (SEQ ID NO.:2).

In another embodiment, the present invention provides a drug delivery device comprising one or more than one multi-use container, which comprises a storage stable composition comprising PTHrP or an analog thereof and an effective amount of buffer to maintain the pH of the composition between 2 and 7. In a particular embodiment, the PTHrP is [Glu$^{22,25}$, Leu$^{23,28,31}$, Aib$^{29}$, Lys$^{26,30}$]hPTHrP(1-34)NH$_2$ (SEQ ID NO.: 2).

In another embodiment the present invention provides a method of treating osteoporosis in a subject in need thereof comprising administering to the subject [Glu$^{22,25}$, Leu$^{23,28,31}$, Aib$^{29}$, Lys$^{26,30}$]hPTHrP(1-34)NH$_2$ (SEQ ID NO.: 2) in an amount between 40 and 160 μg.

In another embodiment the present invention provides a method of increasing bone mass or increasing bone quality in a subject in need thereof comprising administering to the subject [Glu$^{22,25}$, Leu$^{23,28,31}$, Aib$^{29}$, Lys$^{26,30}$]hPTHrP (1-34) NH$_2$ (SEQ ID NO.: 2) in an amount between 40 and 160 m.

The PTHrP compositions of the invention exhibit storage stability in terms of hormone composition and activity. These compositions eliminate the need for chemical stabilizers and other stabilization techniques, such as, lyophilization. Furthermore, these compositions can be administered, in general, in higher dosages than currently available osteoporosis drugs, with the reduction or elimination of unwanted side-effects, such as, hypercalcemia or stimulation of bone resorption. This has the advantage of an increase in beneficial physiological effects due to the increased dosages and can result in a reduction in the length of treatment time.

DETAILED DESCRIPTION OF THE INVENTION

Figure 1:
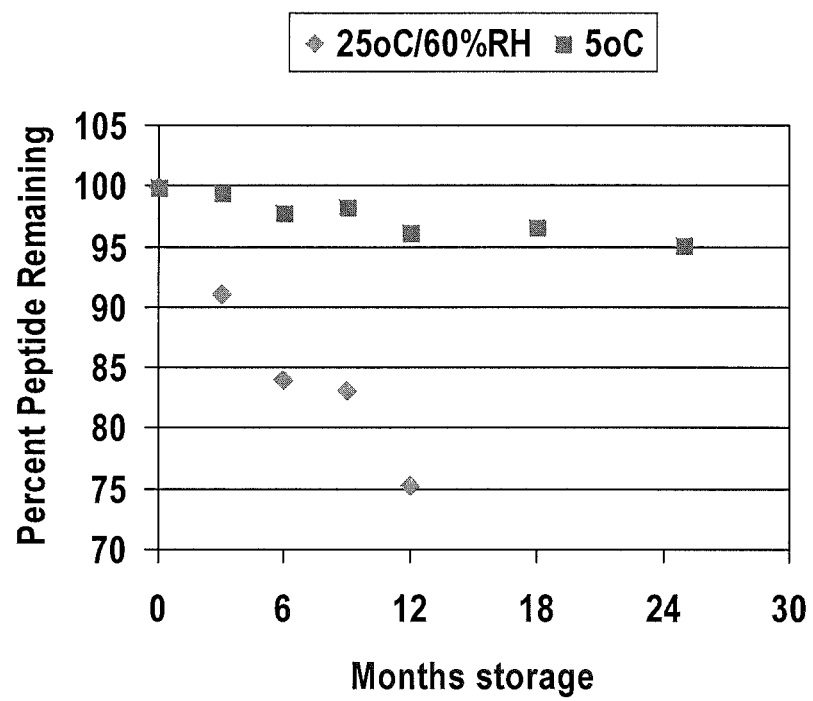
FIG. 1 is a graph showing the stability of SEQ ID NO. 2 over 24 months at 5° C. and 25° C. without any chemical stabilizer.

As used herein "PTHrP" includes analogs and fragments of native human PTHrP. An analog of PTHrP refers to a polypeptide having between about 1 and about 20, between about 1 and about 15, or between about 1 and about 10 art-accepted substitutions, additions or insertions relative to human parathyroid related-hormone protein (hPTHrP), or combinations thereof, not to exceed a total combination of 20 substitutions, additions and insertions. As used herein insertions, include the insertion of an amino acid between two existing amino acids in the peptide chain. As used herein addition means the addition of an amino acid to the N or C terminus of the peptide chain. As used herein substitution means the substitution of an amino acid for an existing amino acid in the peptide chain. As used herein, "art-accepted" substitutions, insertions or additions are those which would maintain or increase and the biological and/or hormonal activity of the peptide and which would not adversely affect the biologically activity of the peptide. Art-accepted includes, for example, substitution of one amino acid with a chemically or biologically similar amino acid, such as a substituting one hydrophobic amino acid for another hydrophobic amino acid. The PTHrPs are described with reference to their variation from the native sequence of human parathyroid hormone-related protein (hPTHrP).

A fragment of PTHrP refers to a polypeptide having a sequence comprising less than the full complement of amino acids found in PTHrP which, however, elicits a similar biological response. The truncated PTHrP fragments may also be analogs as defined above and need not be fully homologous with native PTHrP to elicit a similar biological response.

Typically, the truncated analogs or fragments for use in the methods and compositions of the present invention will be truncated from the C-terminus and will have range from 30 to 40 residues. In particular, hPTHrP(1-34) and analogs with between 1 and 15 substitutions thereof are useful in the methods and compositions of the present invention.

The sequence of native hPTHrP (1-34) is as follows:

(SEQ ID NO: 1)
Ala Val Ser Glu His Gln Leu Leu His Asp Lys Gly Lys Ser Ile Gln Asp Leu Arg
Arg Arg Phe Phe Leu His His Leu Ile Ala Glu Ile His Thr Ala.

In a particular embodiment, the PTHrP is [Glu$^{22,25}$, Leu$^{23,28,31}$, Aib$^{29}$, Lys$^{26,30}$]hPTHrP(1-34)NH$_2$ (SEQ ID NO.: 2).

Other PTHrPs are described in U.S. Pat. Nos. 6,921,750, 5,955,574, 6,544,949, 5,723,577, and 5,696,095 the entire contents of each of which are incorporated herein by reference.

A "buffer" as used herein is any acid or salt combination which is pharmaceutically acceptable and capable of maintaining the composition of the present invention within a desired pH range. Buffers in the disclosed compositions maintain the pH in a range of about 2 to about 7, about 3 to about 6, about 4 to about 6, about 4.5 to about 5.6, or about 5.1. Suitable buffers include, any pharmaceutical acceptable buffer capable of maintaining the above pH ranges, such as, for example, acetate, tartrate phosphate or citrate buffers. In one embodiment, the buffer is an acetate or tartrate buffer. In another embodiment the buffer is an acetate buffer. In one embodiment the buffer is acetic acid and sodium acetate.

In the disclosed compositions the concentration of buffer is typically in the range of about 0.1 mM to about 1000 mM, about 0.2 mM to about 200 mM, about 0.5 mM to about 50 mM, about 1 mM to about 10 mM or about 6 mM.

As used herein, an anti-microbial agent is a pharmaceutically acceptable preservative, suitable for administration to a subject, which inhibits, prevents or delays the growth or micro organisms including, for example bacteria, viruses and fungi in the compositions of the present invention. Suitable anti-microbial agents for use in the compositions and methods of the present invention include, but are not limited to, cresols, benzyl alcohol, phenol, benzalkonium chloride, benzethonium chloride, chlorobutanol, phenylethyl alcohol, methyl paraben, propyl paraben, thiomersal and phenylmercuric nitrate and acetate. In one embodiment the anti-microbial agents is m-cresol, chlorocresol or phenol. In another embodiment the anti-microbial agents is chlorocresol or phenol. In another embodiment the anti-microbial agents is phenol.

As used herein an effective amount of an anti-microbial agent is an amount effective to inhibits, prevents or delays the growth or micro organisms including, for example bacteria, viruses and fungi in the compositions of the present invention. In the compositions of the present invention, the amount of anti-microbial agent is typically in the range from about 0.1 to about 20 mg/ml, about 0.2 to about 30 mg/ml, about 0.2 to about 10 mg/ml, about 0.25 to about 5 mg/ml, about 0.5 to about 50 mg/ml, about 1 to about 10 mg/ml, about 3 mg/ml or about 5 mg/ml.

The compositions of the present invention typically are ready to administer, aqueous solutions which are sterile, storage-stable and pharmaceutically acceptable without the need for reconstitution prior to administration. The compositions of the present invention are suitable for administration to a subject which means that they are pharmaceutically acceptable, non-toxic, do not contain any components which would adversely affect the biological or hormonal effects of the peptide. The compositions of the present invention do not, for example, comprise any cells.

As used herein a composition of the present invention is storage-stable if the amount, purity of the PTHrP remains above about 95% of the original amount under one of the following conditions: (1) storage for over 2 years at 5° C.; or (2) storage for over 30 days at 25° C.

The compositions are typically stored in a sealed container, vial or cartridge which is typically suitable for long term storage. "Suitable for long-term storage" means that the vial, container or cartridge does not allow for the escape of components of the compositions of the present invention or the ingress of external components, such as, micro organisms when kept for at least 3 months at 25° C.

The compositions of the present invention can be administered by injection, typically subcutaneous injection.

The compositions of the present invention, can be stored in single-dose or multi-dose sealed containers, vials or cartridges. The sealed container, vial or cartridge is typically suitable for use with a single or multi-dose injection pen or drug delivery device, which typically allows the patient to administer the peptide themselves. The sealed container can comprise one or more doses of the peptide of the present invention, wherein each dose comprises an effective amount of the peptide as described herein.

A single-dose injection pen, or drug delivery device is typically a disposable device which uses a sealed container which comprises a single dose of an effective amount of a PTHrP in the compositions described herein. A multi-dose injection pen or drug delivery device typically contains more than one dose of an effective amount of a PTHrP thereof in the compositions described herein. The multi-dose pen can typically be adjusted to administer the desired volume of the storage stable compositions described herein. In certain embodiment the multi-dose injection pen prevents the ingress of microbial contaminants from entering the container or cartridge which can occur through multiple uses of one needle.

Injection pens, as used herein, can also comprise two containers one of which contains a PTHrP, as described herein, in a lyophilized powder, as described below, and the second container contains a liquid for reconstitution of the lyophilized powder. The contents of the two containers can be mixed prior to administration.

As discussed above the compositions of the present invention can be administered by injection. Suitable volumes of the compositions of the present invention for injection include about 0.5 to about 1 ml, about 0.1 to about 1 ml, about 0.02-to about 0.04 ml, about 0.1-to about 5.0 µl, or about 0.1-to about 1.0 µl.

In the compositions of the present invention the concentration of the peptides is from about 20 ug/ml to about 20,000 ug/ml, from about 100 ug/ml to about 10,000 ug/ml, from about 300 ug/ml to about 3000 ug/ml, from about 500 ug/ml to about 2000 ug/ml and about 2 mg/ml.

The compositions of the present invention can also be lyophilized using lyophilization techniques known in the art and stored as a powder which can be reconstituted prior to administration. The term "lyophilization" as used herein is a freeze drying or dehydration technique which involves removing a solvent, preferably a water miscible solvent, more preferably water from a composition or the present invention, typically by sublimation under high vacuum when the composition is in a frozen state. Typically, lyophilization is carried out in lyophilization equipment (a lyophilizer), which comprises a drying chamber with variable temperature controls, a condenser to collect water, and a vacuum system to reduce the pressure in the drying chamber.

The terms "lyophilized composition", as used herein mean the solid residue or powder which is produced or which remains after the lyophilization procedure as defined above. The lyophilized composition of the present invention typically further comprise a pharmaceutically acceptable excipient. The term "pharmaceutically acceptable excipient" as used herein refers to a substance which is added to a solution prior to lyophilization to enhance characteristics such as the color, texture, strength, and volume of the lyophilized cake. Pharmaceutically acceptable excipients may be, for example, buffers and pH adjusters, crystalline bulking excipients, stabilizers, and tonicity raising agents.

In certain preferred embodiments the pharmaceutically acceptable excipient is a crystalline bulking excipient. The terms "crystalline bulking excipient" or "crystalline bulking agent" as used herein means an excipient which provides bulk and structure to the lyophilization cake. These crystalline bulking agents are inert and do not react with the peptide. In addition, the crystalline bulking agents are capable of crystallizing under lyophilization conditions.

Examples of suitable crystalline bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, glucose, fructose, gulose, idose, galactose, talose, ribose, arabinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats and polyvinylpyrrolidone. Preferred crystalline bulking agents are selected from the group consisting of glycine, mannitol, dextran, dextrose, lactose, sucrose, polyvinylpyrrolidone, trehalose, glucose and combinations thereof. Particularly useful bulking agents include dextran.

As used herein a stabilizer is a composition which maintains the chemical, biological or hormonal stability of the peptide. Examples of stabilizing agent include polyols which includes a saccharide, preferably a monosaccharide or disaccharide, e.g., glucose, trehalose, raffinose, or sucrose; a sugar alcohol such as, for example, mannitol, sorbitol or inositol, a polyhydric alcohol such as glycerine or propylene glycol or mixtures thereof and albumin.

The compositions described herein can be used to stimulate bone growth in a subject. Thus they are useful in the treatment of diseases or disorders associated with deficiency in bone growth such as osteoporosis and bone fractures. In one embodiment, the present invention is a method of treating osteoporosis in a subject comprising administering to the subject an effective amount of composition described herein.

As used herein, "treating" can include both prophylactic, and therapeutic treatment. For example, therapeutic treatment can include delaying inhibiting or preventing the progression of osteoporosis, the reduction or elimination of symptoms associated with osteoporosis. Prophylactic treatment can include preventing, inhibiting or delaying the onset of osteoporosis.

As used herein, an effective amount refers to an amount sufficient to elicit the desired response. In the present invention, the desired biological response is a decrease in the rate of bone loss and/or an increase in the bone mass or bone quality of a subject.

Suitable dosage for use in the compositions and methods of the present invention include from about 40 to about 160 µg, about 80 to about 120 µg about 80 to about 100 µg; or from about 40 to about 50 µg, about 50 to about 60 µg, about 60 to about 70 µg, about 70 to about 80 µg, about 80 to about 90 µg, about 90 to about 100 µg, about 100 to about 110 µg, about 110 to about 120 µg, about 120 to about 130 µg, about 130 to about 140 µg, about 140 to about 150 µg, about 150 to about 160 µg; or from 40 to about 45 µg, about 45 to about 50 µg, about 50 to about 55 µg, about 55 to about 60 µg, about 60 to about 65 µg, about 65 to about 70 µg, about 70 to about 75 µg, about 75 to about 80 µg, about 80 to about 85 µg, about 85 to about 90 µg, about 90 to about 95 µg, about 95 to about 100 µg, about 100 to about 105 µg, about 105 to about 110 µg, about 110 to about 115 µg, about 115 to about 120 µg, about 120 to about 125 µg, about 125 to about 130 µg, about 130 to about 135 µg, about 135 to about 140 µg, about 140 to about 145 µg, about 145 to about 150 µg, about 150 to about 155 µg, about 155 to about 160 µg administered once per day, once every other day, twice per week once per week, once every two weeks, once per month. The doses can be a pulsatile injection, for example, once per month which causes pulsatile release of singles doses of the composition described herein.

When the dosages described above are administered once per day, once per week etc., typically the dosages are of equal amounts.

The subject as used herein can be an animal, for example, a mammal, such as a human.

In certain embodiments of this invention, compositions comprising dosage forms containing 20 µg, 40 µg, or 80 µg of [Glu$^{22,25}$, Leu$^{23,28,31}$, Aib$^{29}$, Lys$^{26,30}$]hPTHrP(1-34)NH$_2$ (SEQ ID NO.: 2) are described.

In certain embodiments of this invention, a method of treatment of osteoporosis is described wherein doses of 20 µg, 40 µg, or 80 µg of [Glu$^{22,25}$, Leu$^{23,28,31}$, Aib$^{29}$, Lys$^{26,30}$] hPTHrP(1-34)NH$_2$ (SEQ ID NO.: 2) are administered by daily subcutaneous injection to a subject in need thereof.

In some embodiments, the subject in need thereof has osteoporosis.

In some embodiments, the subject in need thereof has osteopenia.

In certain embodiments, the subject in need thereof is a post-menopausal woman.

In some embodiments, the subject in need thereof has glucocorticoid induced osteoporosis.

In certain embodiments, the subject in need thereof has glucocorticoid induced osteopenia.

In some embodiments this invention provides a method of treatment of osteoporosis comprising treating a subject in need thereof by daily subcutaneous injection of SEQ ID NO. 2 resulting in plasma Cmax levels of SEQ ID NO. 2 between 32.4 pg/mL and 53.8 pg/mL.

In some embodiments this invention provides a method of treatment of osteoporosis comprising treating a subject in need thereof by daily subcutaneous injection of 5 µg SEQ ID NO. 2 resulting in plasma Cmax levels of SEQ ID NO. 2 between 32.4 pg/mL and 53.8 pg/mL.

In some embodiments this invention provides a method of treatment of osteoporosis comprising treating a subject in need thereof by daily subcutaneous injection of SEQ ID NO. 2 resulting in plasma Cmax levels of SEQ ID NO. 2 between 61.1 pg/mL and 168.9 pg/mL.

In some embodiments this invention provides a method of treatment of osteoporosis comprising treating a subject in need thereof by daily subcutaneous injection of 20 µg SEQ ID NO. 2 resulting in plasma Cmax levels of SEQ ID NO. 2 between 61.1 pg/mL and 168.9 pg/mL.

In some embodiments this invention provides a method of treatment of osteoporosis comprising treating a subject in need thereof by daily subcutaneous injection of SEQ ID NO. 2 resulting in plasma Cmax levels of SEQ ID NO. 2 between 124 pg/mL and 322 pg/mL.

In some embodiments this invention provides a method of treatment of osteoporosis comprising treating a subject in need thereof by daily subcutaneous injection of 40 uG SEQ ID NO. 2 resulting in plasma Cmax levels of SEQ ID NO. 2 between 124 pg/mL and 322 pg/mL.

In some embodiments this invention provides a method of treatment of osteoporosis comprising treating a subject in need thereof by daily subcutaneous injection of SEQ ID NO. 2 resulting in Cmax plasma levels of SEQ ID NO. 2 between 255.57 pg/mL and 364.3 pg/mL.

In some embodiments this invention provides a method of treatment of osteoporosis comprising treating a subject in need thereof by daily subcutaneous injection of 80 µg SEQ ID NO. 2 resulting in Cmax plasma levels of SEQ ID NO. 2 between 255.57 pg/mL and 364.3 pg/mL.

In some embodiments this invention provides a method of treatment of osteoporosis comprising treating a subject in need thereof by daily subcutaneous injection of SEQ ID NO. 2 resulting in a plasma T$_{max}$ for SEQ ID NO. 2 between 0.531 hours and 1.00 hours.

In some embodiments this invention provides a method of treatment of osteoporosis comprising treating a subject in need thereof by daily subcutaneous injection of 5 µg SEQ ID NO. 2 resulting in a plasma T$_{max}$ for SEQ ID NO. 2 between 0.531 hours and 1.00 hours.

In some embodiments this invention provides a method of treatment of osteoporosis comprising treating a subject in need thereof by daily subcutaneous injection of SEQ ID NO. 2 resulting in a plasma T$_{max}$ for SEQ ID NO. 2 between 0.250 hours and 0.624 hours.

In some embodiments this invention provides a method of treatment of osteoporosis comprising treating a subject in need thereof by daily subcutaneous injection of 20 µg SEQ ID NO. 2 resulting in a plasma T$_{max}$ for SEQ ID NO. 2 between 0.250 hours and 0.624 hours.

In some embodiments this invention provides a method of treatment of osteoporosis comprising treating a subject in need thereof by daily subcutaneous injection of SEQ ID NO. 2 resulting in a plasma T$_{max}$ for SEQ ID NO. 2 between 0.262 hours and 0.579 hours.

In some embodiments this invention provides a method of treatment of osteoporosis comprising treating a subject in need thereof by daily subcutaneous injection of 40 µg SEQ ID NO. 2 resulting in a plasma T$_{max}$ for SEQ ID NO. 2 between 0.262 hours and 0.579 hours.

In some embodiments this invention provides a method of treatment of osteoporosis comprising treating a subject in need thereof by daily subcutaneous injection of SEQ ID NO. 2 resulting in a plasma T$_{max}$ for SEQ ID NO. 2 between 0.251 hours and 1.01 hours.

In some embodiments this invention provides a method of treatment of osteoporosis comprising treating a subject in need thereof by daily subcutaneous injection of 80 µg SEQ ID NO. 2 resulting in a plasma T$_{max}$ for SEQ ID NO. 2 between 0.251 hours and 1.01 hours.

In some embodiments this invention provides a method of treatment of osteoporosis comprising treating a subject in need thereof by daily subcutaneous injection of SEQ ID NO. 2 resulting in a plasma t$_{1/2}$ of SEQ ID NO. 2 between 1.90 hours and 3.28 hours.

In some embodiments this invention provides a method of treatment of osteoporosis comprising treating a subject in need thereof by daily subcutaneous injection of 5 µg SEQ ID NO. 2 resulting in a plasma t$_{1/2}$ of SEQ ID NO. 2 between 1.90 hours and 3.28 hours.

In some embodiments this invention provides a method of treatment of osteoporosis comprising treating a subject in need thereof by daily subcutaneous injection of SEQ ID NO. 2 resulting in a plasma t$_{1/2}$ of SEQ ID NO. 2 between 0.736 hours and 1.364 hours.

In some embodiments this invention provides a method of treatment of osteoporosis comprising treating a subject in need thereof by daily subcutaneous injection of 20 µg SEQ ID NO. 2 resulting in a plasma t$_{1/2}$ of SEQ ID NO. 2 between 0.736 hours and 1.364 hours.

In some embodiments this invention provides a method of treatment of osteoporosis comprising treating a subject in need thereof by daily subcutaneous injection of SEQ ID NO. 2 resulting in a plasma t$_{1/2}$ of SEQ ID NO. 2 between 1.396 hours and 1.904 hours.

In some embodiments this invention provides a method of treatment of osteoporosis comprising treating a subject in need thereof by daily subcutaneous injection of 40 µg SEQ ID NO. 2 resulting in a plasma t$_{1/2}$ of SEQ ID NO. 2 between 1.396 hours and 1.904 hours.

In some embodiments this invention provides a method of treatment of osteoporosis comprising treating a subject in need thereof by daily subcutaneous injection of SEQ ID NO. 2 resulting in a plasma $t_{1/2}$, of SEQ ID NO. 2 between 1.585 hours and 3.015 hours.

In some embodiments this invention provides a method of treatment of osteoporosis comprising treating a subject in need thereof by daily subcutaneous injection of 80 μg SEQ ID NO. 2 resulting in a plasma $t_{1/2}$ of SEQ ID NO. 2 between 1.585 hours and 3.015 hours.

In some embodiments this invention provides a method of treatment of osteoporosis comprising treating a subject in need thereof by daily subcutaneous injection of SEQ ID NO. 2 resulting in a net plasma $AUC_{(0\text{-}inf)}$ of SEQ ID NO. 2 between 132.82 pg h/mL and 241.90 pg h/mL.

In some embodiments this invention provides a method of treatment of osteoporosis comprising treating a subject in need thereof by daily subcutaneous injection of 5 μg of SEQ ID NO. 2 resulting in a net plasma $AUC_{(0\text{-}inf)}$ of SEQ ID NO. 2 between 132.82 pg h/mL and 241.90 pg h/mL.

In some embodiments this invention provides a method of treatment of osteoporosis comprising treating a subject in need thereof by daily subcutaneous injection of SEQ ID NO. 2 resulting in a net plasma $AUC_{(0\text{-}inf)}$ of SEQ ID NO. 2 between 138.12 pg h/mL and 376.22 pg h/mL.

In some embodiments this invention provides a method of treatment of osteoporosis comprising treating a subject in need thereof by daily subcutaneous injection of 20 μg of SEQ ID NO. 2 resulting in a net plasma $AUC_{(0\text{-}inf)}$ of SEQ ID NO. 2 between 138.12 pg h/mL and 376.22 pg h/mL.

In some embodiments this invention provides a method of treatment of osteoporosis comprising treating a subject in need thereof by daily subcutaneous injection of SEQ ID NO. 2 resulting in a net plasma $AUC_{(0\text{-}inf)}$ of SEQ ID NO. 2 between 311.54 pg h/mL and 874.34 pg h/mL.

In some embodiments this invention provides a method of treatment of osteoporosis comprising treating a subject in need thereof by daily subcutaneous injection of 40 μg of SEQ ID NO. 2 resulting in a net plasma $AUC_{(0\text{-}inf)}$ of SEQ ID NO. 2 between 311.54 pg h/mL and 874.34 pg h/mL.

In some embodiments this invention provides a method of treatment of osteoporosis comprising treating a subject in need thereof by daily subcutaneous injection of SEQ ID NO. 2 resulting in a net plasma $AUC_{(0\text{-}inf)}$ of SEQ ID NO. 2 between 541.99 pg h/mL and 1569.21 pg h/mL.

In some embodiments this invention provides a method of treatment of osteoporosis comprising treating a subject in need thereof by daily subcutaneous injection of 80 μg of SEQ ID NO. 2 resulting in a net plasma $AUC_{(0\text{-}inf)}$ of SEQ ID NO. 2 between 541.99 pg h/mL and 1569.21 pg h/mL.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 33.2 pg/mL and 48.4 pg/mL.

In some embodiments this invention provides a method of treatment of osteoporosis comprising treating a subject in need thereof by daily subcutaneous injection of 5 μg SEQ ID NO. 2 resulting in a plasma Cmax level of SEQ ID NO. 2 between 33.2 pg/mL and 48.4 pg/mL.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 89.8 pg/mL and 128.2 pg/mL.

In some embodiments this invention provides a method of treatment of osteoporosis comprising treating a subject in need thereof by daily subcutaneous injection of 20 μg SEQ ID NO. 2 resulting in a plasma Cmax level of SEQ ID NO. 2 between 89.8 pg/mL and 128.2 pg/mL.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 129.3 pg/mL and 284.4 pg/mL.

In some embodiments this invention provides a method of treatment of osteoporosis comprising treating a subject in need thereof by daily subcutaneous injection of 40 uG SEQ ID NO. 2 resulting in a plasma Cmax level of SEQ ID NO. 2 between 129.3 pg/mL and 284.4 pg/mL.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 367.2 pg/mL and 504.8 pg/mL.

In some embodiments this invention provides a method of treatment of osteoporosis comprising treating a subject in need thereof by daily subcutaneous injection of 80 μg SEQ ID NO. 2 resulting in a plasma Cmax level of SEQ ID NO. 2 between 367.2 pg/mL and 504.8 pg/mL.

In some embodiments this invention provides a method of treatment of osteoporosis comprising treating a subject in need thereof by daily subcutaneous injection of SEQ ID NO. 2 resulting in a plasma $T_{max}$ for SEQ ID NO. 2 between 0.514 hours and 1.53 hours.

In some embodiments this invention provides a method of treatment of osteoporosis comprising treating a subject in need thereof by daily subcutaneous injection of 5 μg SEQ ID NO. 2 resulting in a plasma $T_{max}$ for SEQ ID NO. 2 between 0.514 hours and 1.53 hours.

In some embodiments this invention provides a method of treatment of osteoporosis comprising treating a subject in need thereof by daily subcutaneous injection of SEQ ID NO. 2 resulting in a plasma $T_{max}$ for SEQ ID NO. 2 between 0.250 hours and 3.05 hours.

In some embodiments this invention provides a method of treatment of osteoporosis comprising treating a subject in need thereof by daily subcutaneous injection of 20 μg SEQ ID NO. 2 resulting in a plasma $T_{max}$ for SEQ ID NO. 2 between 0.250 hours and 3.05 hours.

In some embodiments this invention provides a method of treatment of osteoporosis comprising treating a subject in need thereof by daily subcutaneous injection of SEQ ID NO. 2 resulting in a plasma $T_{max}$ for SEQ ID NO. 2 between 0.349 hours and 1.00 hours.

In some embodiments this invention provides a method of treatment of osteoporosis comprising treating a subject in need thereof by daily subcutaneous injection of 40 μg SEQ ID NO. 2 resulting in a plasma $T_{max}$ for SEQ ID NO. 2 between 0.349 hours and 1.00 hours.

In some embodiments this invention provides a method of treatment of osteoporosis comprising treating a subject in need thereof by daily subcutaneous injection of SEQ ID NO. 2 resulting in a plasma $T_{max}$ for SEQ ID NO. 2 between 0.500 hours and 1.00 hours.

In some embodiments this invention provides a method of treatment of osteoporosis comprising treating a subject in need thereof by daily subcutaneous injection of 80 μg SEQ ID NO. 2 resulting in a plasma $T_{max}$ for SEQ ID NO. 2 between 0.500 hours and 1.00 hours.

In some embodiments this invention provides a method of treatment of osteoporosis comprising treating a subject in need thereof by daily subcutaneous injection of SEQ ID NO. 2 resulting in a plasma $t_{1/2}$ of SEQ ID NO. 2 between 0.806 hours and 1.294 hours.

In some embodiments this invention provides a method of treatment of osteoporosis comprising treating a subject in need thereof by daily subcutaneous injection of 20 μg SEQ ID NO. 2 resulting in a plasma $t_{1/2}$ of SEQ ID NO. 2 between 0.806 hours and 1.294 hours.

In some embodiments this invention provides a method of treatment of osteoporosis comprising treating a subject in need thereof by daily subcutaneous injection of SEQ ID NO. 2 resulting in a plasma $t_{1/2}$ of SEQ ID NO. 2 between 1.033 hours and 1.827 hours.

In some embodiments this invention provides a method of treatment of osteoporosis comprising treating a subject in need thereof by daily subcutaneous injection of 40 μg SEQ ID NO. 2 resulting in a plasma $t_{1/2}$ of SEQ ID NO. 2 between 1.033 hours and 1.827 hours.

In some embodiments this invention provides a method of treatment of osteoporosis comprising treating a subject in need thereof by daily subcutaneous injection of SEQ ID NO. 2 resulting in a plasma $t_{1/2}$ of SEQ ID NO. 2 between 1.265 hours and 2.115 hours.

In some embodiments this invention provides a method of treatment of osteoporosis comprising treating a subject in need thereof by daily subcutaneous injection of 80 μg SEQ ID NO. 2 resulting in a plasma $t_{1/2}$ of SEQ ID NO. 2 between 1.265 hours and 2.115 hours.

In some embodiments this invention provides a method of treatment of osteoporosis comprising treating a subject in need thereof by daily subcutaneous injection of SEQ ID NO. 2 resulting in a net plasma $AUC_{(0-2.5h)}$ of SEQ ID NO. 2 between 50.263 pg h/mL and 111.14 pg h/mL.

In some embodiments this invention provides a method of treatment of osteoporosis comprising treating a subject in need thereof by daily subcutaneous injection of 5 μg of SEQ ID NO. 2 resulting in a net plasma $AUC_{(0-2.5h)}$ of SEQ ID NO. 2 between 50.263 pg h/mL and 111.14 pg h/mL.

In some embodiments this invention provides a method of treatment of osteoporosis comprising treating a subject in need thereof by daily subcutaneous injection of SEQ ID NO. 2 resulting in a net plasma $AUC_{(0-3.0h)}$ of SEQ ID NO. 2 between 89.549 pg h/mL and 253.611 pg h/mL.

In some embodiments this invention provides a method of treatment of osteoporosis comprising treating a subject in need thereof by daily subcutaneous injection of 20 μg of SEQ ID NO. 2 resulting in a net plasma $AUC_{(0-3.0h)}$ of SEQ ID NO. 2 between 89.549 pg h/mL and 253.611 pg h/mL.

In some embodiments this invention provides a method of treatment of osteoporosis comprising treating a subject in need thereof by daily subcutaneous injection of SEQ ID NO. 2 resulting in a net plasma $AUC_{(0-3.49h)}$ of SEQ ID NO. 2 between 188.28 pg h/mL and 627.68 pg h/mL.

In some embodiments this invention provides a method of treatment of osteoporosis comprising treating a subject in need thereof by daily subcutaneous injection of 40 μg of SEQ ID NO. 2 resulting in a net plasma $AUC_{(0-3.49h)}$ of SEQ ID NO. 2 between 188.28 pg h/mL and 627.68 pg h/mL.

In some embodiments this invention provides a method of treatment of osteoporosis comprising treating a subject in need thereof by daily subcutaneous injection of SEQ ID NO. 2 resulting in a net plasma $AUC_{(0-6.00h)}$ of SEQ ID NO. 2 between 619.55 pg h/mL and 1386.45 pg h/mL.

In some embodiments this invention provides a method of treatment of osteoporosis comprising treating a subject in need thereof by daily subcutaneous injection of 80 μg of SEQ ID NO. 2 resulting in a net plasma $AUC_{(0-6.00h)}$ of SEQ ID NO. 2 between 619.55 pg h/mL and 1386.45 pg h/mL.

In some embodiments this invention provides a method of treatment of osteoporosis comprising treating a subject in need thereof by daily subcutaneous injection of 5 μg SEQ ID NO. 2 resulting in a plasma Cmax level between 32.4 pg/mL and 53.8 pg/mL of SEQ ID NO. 2 and a plasma $T_{max}$ for SEQ ID NO. 2 between 0.531 hours and 1.00 hours.

In some embodiments this invention provides a method of treatment of osteoporosis comprising treating a subject in need thereof by daily subcutaneous injection of SEQ ID NO. 2 resulting in a plasma Cmax level between 61.1 pg/mL and 168.9 pg/mL of SEQ ID NO. 2 and a plasma $T_{max}$ for SEQ ID NO. 2 between 0.25 hours and 0.624 hours.

In some embodiments this invention provides a method of treatment of osteoporosis comprising treating a subject in need thereof by daily subcutaneous injection of 20 μg SEQ ID NO. 2 resulting in a plasma Cmax level between 61.1 pg/mL and 168.9 pg/mL of SEQ ID NO. 2 and a plasma $T_{max}$ for SEQ ID NO. 2 between 0.25 hours and 0.624 hours.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 124 pg/mL and 322 pg/mL and a plasma $T_{max}$ for SEQ ID NO. 2 for SEQ ID NO. 2 between 0.262 hours and 0.579 hours.

In some embodiments this invention provides a method of treatment of osteoporosis comprising treating a subject in need thereof by daily subcutaneous injection of 40 μg SEQ ID NO. 2 resulting in a plasma Cmax level of SEQ ID NO. 2 between 124 pg/mL and 322 pg/mL and a plasma $T_{max}$ for SEQ ID NO. 2 between 0.262 hours and 0.579 hours.

In some embodiments this invention provides a method of treatment of osteoporosis comprising treating a subject in need thereof by daily subcutaneous injection of SEQ ID NO. 2 resulting in a Cmax plasma level of SEQ ID NO. 2 between 255.57 pg/mL and 364.3 pg/mL and a plasma $T_{max}$ for SEQ ID NO. 2 of between 0.251 hours and 1.01 hours.

In some embodiments this invention provides a method of treatment of osteoporosis comprising treating a subject in need thereof by daily subcutaneous injection of 80 μg SEQ ID NO. 2 resulting in a Cmax plasma level between 255.57 pg/mL and 364.3 pg/mL and a plasma $T_{max}$ for SEQ ID NO. 2 between 0.251 hours and 1.01 hours.

In some embodiments this invention provides a method of treatment of osteoporosis comprising treating a subject in need thereof by daily subcutaneous injection of 5 μg SEQ ID NO. 2 resulting in a plasma Cmax level between 33.2 pg/mL and 48.4 pg/mL of SEQ ID NO. 2 and a plasma $T_{max}$ for SEQ ID NO. 2 between 0.514 hours and 1.53 hours.

In some embodiments this invention provides a method of treatment of osteoporosis comprising treating a subject in need thereof by daily subcutaneous injection of SEQ ID NO. 2 resulting in a plasma Cmax level between 89.8 pg/mL and 128.2 pg/mL of SEQ ID NO. 2 and a plasma $T_{max}$ for SEQ ID NO. 2 between 0.250 hours and 3.05 hours.

In some embodiments this invention provides a method of treatment of osteoporosis comprising treating a subject in need thereof by daily subcutaneous injection of 20 μg SEQ ID NO. 2 resulting in a plasma Cmax level between 89.8 pg/mL and 128.2 pg/mL of SEQ ID NO. 2 and a plasma $T_{max}$ for SEQ ID NO. 2 between 0.250 hours and 3.05 hours.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 129.3 pg/mL and 284.4 pg/mL and a plasma $T_{max}$ for SEQ ID NO. 2 for SEQ ID NO. 2 between 0.349 hours and 1.00 hours.

In some embodiments this invention provides a method of treatment of osteoporosis comprising treating a subject in need thereof by daily subcutaneous injection of 40 μg SEQ ID NO. 2 resulting in a plasma Cmax level of SEQ ID NO. 2 between 129.3 pg/mL and 284.4 pg/mL and a plasma $T_{max}$ for SEQ ID NO. 2 between 0.349 hours and 1.00 hours.

In some embodiments this invention provides a method of treatment of osteoporosis comprising treating a subject in need thereof by daily subcutaneous injection of SEQ ID NO. 2 resulting in a Cmax plasma level of SEQ ID NO. 2 between 367.2 pg/mL and 504.8 pg/mL and a plasma $T_{max}$ for SEQ ID NO. 2 of between 0.500 hours and 1.00 hours.

In some embodiments this invention provides a method of treatment of osteoporosis comprising treating a subject in need thereof by daily subcutaneous injection of 80 µg SEQ ID NO. 2 resulting in a Cmax plasma level between 367.2 pg/mL and 504.8 pg/mL and a plasma $T_{max}$ for SEQ ID NO. 2 between 0.500 hours and 1.00 hours.

In some embodiments this invention provides a method of treatment of osteoporosis comprising treating a subject in need thereof by daily subcutaneous injection of 5 µg SEQ ID NO. 2 resulting in a plasma Cmax level between 32.4 pg/mL and 53.8 pg/mL of SEQ ID NO. 2, a plasma $T_{max}$ for SEQ ID NO. 2 between 0.531 hours and 1.00 hours and a plasma $t_{1/2}$ for SEQ ID NO. 2 of between 1.90 and 3.28 hours.

In some embodiments this invention provides a method of treatment of osteoporosis comprising treating a subject in need thereof by daily subcutaneous injection of SEQ ID NO. 2 resulting in a plasma Cmax level between 61.1 pg/mL and 168.9 pg/mL of SEQ ID NO. 2, a plasma $T_{max}$ for SEQ ID NO. 2 between 0.25 hours and 0.624 hours and a plasma $t_{1/2}$ for SEQ ID NO. 2 of between 0.736 hours and 1.364 hours.

In some embodiments this invention provides a method of treatment of osteoporosis comprising treating a subject in need thereof by daily subcutaneous injection of 20 pg SEQ ID NO. 2 resulting in a plasma Cmax level between 61.1 pg/mL and 168.9 pg/mL of SEQ ID NO. 2 and a plasma $T_{max}$ for SEQ ID NO. 2 between 0.25 hours and 0.624 hours and a plasma $t_{1/2}$ for SEQ ID NO. 2 of between 0.736 hours and 1.364 hours.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 124 pg/mL and 322 pg/mL and a plasma $T_{max}$ for SEQ ID NO. 2 for SEQ ID NO. 2 between 0.262 hours and 0.579 hours and a plasma $t_{1/2}$ for SEQ ID NO. 2 of between 1.396 hours and 1.904 hours.

In some embodiments this invention provides a method of treatment of osteoporosis comprising treating a subject in need thereof by daily subcutaneous injection of 40 pg SEQ ID NO. 2 resulting in a plasma Cmax level of SEQ ID NO. 2 between 124 pg/mL and 322 pg/mL and a plasma $T_{max}$ for SEQ ID NO. 2 between 0.262 hours and 0.579 hours and a plasma $t_{1/2}$, for SEQ ID NO. 2 of between 0.736 hours and 1.364 hours.

In some embodiments this invention provides a method of treatment of osteoporosis comprising treating a subject in need thereof by daily subcutaneous injection of SEQ ID NO. 2 resulting in a Cmax plasma level of SEQ ID NO. 2 between 255.57 pg/mL and 364.3 pg/mL and a plasma $T_{max}$ for SEQ ID NO. 2 of between 0.251 hours and 1.01 hours and a plasma $t_{1/2}$ for SEQ ID NO. 2 of between 1.585 hours and 3.015 hours.

In some embodiments this invention provides a method of treatment of osteoporosis comprising treating a subject in need thereof by daily subcutaneous injection of 80 µg SEQ ID NO. 2 resulting in a Cmax plasma level between 255.57 pg/mL and 364.3 pg/mL and a plasma $T_{max}$ for SEQ ID NO. 2 between 0.251 hours and 1.01 hours and a plasma $t_{1/2}$ for SEQ ID NO. 2 of between 1.585 hours and 3.015 hours.

In some embodiments this invention provides a method of treatment of osteoporosis comprising treating a subject in need thereof by daily subcutaneous injection of SEQ ID NO. 2 resulting in a plasma Cmax level between 89.8 pg/mL and 128.2 pg/mL of SEQ ID NO. 2 and a plasma $T_{max}$ for SEQ ID NO. 2 between 0.250 hours and 3.05 hours and a plasma $t_{1/2}$ for SEQ ID NO. 2 of between 0.806 hours and 1.294 hours.

In some embodiments this invention provides a method of treatment of osteoporosis comprising treating a subject in need thereof by daily subcutaneous injection of 20 µg SEQ ID NO. 2 resulting in a plasma Cmax level between 89.8 pg/mL and 128.2 pg/mL of SEQ ID NO. 2 and a plasma $T_{max}$ for SEQ ID NO. 2 between 0.250 hours and 3.05 hours and a plasma $t_{1/2}$ for SEQ ID NO. 2 of between 0.806 hours and 1.294 hours.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 129.3 pg/mL and 284.4 pg/mL and a plasma $T_{max}$ for SEQ ID NO. 2 for SEQ ID NO. 2 between 0.349 hours and 1.00 hours and a plasma $t_{1/2}$ for SEQ ID NO. 2 of between 1.033 hours and 1.827 hours.

In some embodiments this invention provides a method of treatment of osteoporosis comprising treating a subject in need thereof by daily subcutaneous injection of 40 µg SEQ ID NO. 2 resulting in a plasma Cmax level of SEQ ID NO. 2 between 129.3 pg/mL and 284.4 pg/mL and a plasma $T_{max}$ for SEQ ID NO. 2 between 0.349 hours and 1.00 hours and a plasma $t_{1/2}$ for SEQ ID NO. 2 of between 1.033 hours and 1.827 hours.

In some embodiments this invention provides a method of treatment of osteoporosis comprising treating a subject in need thereof by daily subcutaneous injection of SEQ ID NO. 2 resulting in a Cmax plasma level of SEQ ID NO. 2 between 367.2 pg/mL and 504.8 pg/mL and a plasma $T_{max}$ for SEQ ID NO. 2 of between 0.500 hours and 1.00 hours and a plasma $t_{1/2}$ for SEQ ID NO. 2 of between 1.265 hours and 2.115 hours.

In some embodiments this invention provides a method of treatment of osteoporosis comprising treating a subject in need thereof by daily subcutaneous injection of 80 µg SEQ ID NO. 2 resulting in a Cmax plasma level between 367.2 pg/mL and 504.8 pg/mL and a plasma $T_{max}$ for SEQ ID NO. 2 between 0.500 hours and 1.00 hours and a plasma $t_{1/2}$ for SEQ ID NO. 2 of between 1.265 hours and 2.115 hours.

In some embodiments this invention provides a method of treatment of osteoporosis comprising treating a subject in need thereof by daily subcutaneous injection of SEQ ID NO. 2 resulting in a plasma Cmax level between 61.1 pg/mL and 168.9 pg/mL of SEQ ID NO. 2, a plasma $T_{max}$ for SEQ ID NO. 2 between 0.25 hours and 0.624 hours, a plasma $t_{1/2}$ for SEQ ID NO. 2 of between 0.736 hours and 1.364 hours and a net plasma $AUC_{(0-inf)}$ of SEQ ID NO. 2 between 138.12 pg h/mL and 376.22 pg h/mL.

In some embodiments this invention provides a method of treatment of osteoporosis comprising treating a subject in need thereof by daily subcutaneous injection of 20 µg SEQ ID NO. 2 resulting in a plasma Cmax level between 61.1 pg/mL and 168.9 pg/mL of SEQ ID NO. 2 and a plasma $T_{max}$ for SEQ ID NO. 2 between 0.25 hours and 0.624 hours, a plasma $t_{1/2}$ for SEQ ID NO. 2 of between 0.736 hours and 1.364 hours and a net plasma $AUC_{(0-inf)}$ of SEQ ID NO. 2 between 138.12 pg h/mL and 376.22 pg h/mL.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 124 pg/mL and 322 pg/mL, a plasma $T_{max}$ for SEQ ID NO. 2 between 0.262 hours and 0.579 hours, a plasma $t_{1/2}$ for SEQ ID NO. 2 of between 1.396 hours and 1.904 hours and a net plasma $AUC_{(0\text{-}inf)}$ of SEQ ID NO. 2 between 311.54 pg h/mL and 874.34 pg h/mL.

In some embodiments this invention provides a method of treatment of osteoporosis comprising treating a subject in need thereof by daily subcutaneous injection of 40 µg SEQ ID NO. 2 resulting in a plasma Cmax level of SEQ ID NO. 2 between 124 pg/mL and 322 pg/mL, a plasma $T_{max}$ for SEQ ID NO. 2 between 0.262 hours and 0.579 hours, a plasma $t_{1/2}$ for SEQ ID NO. 2 of between 0.736 hours and 1.364 hours and a net plasma $AUC_{(0\text{-}inf)}$ of SEQ ID NO. 2 between 311.54 pg h/mL and 874.34 pg h/mL.

In some embodiments this invention provides a method of treatment of osteoporosis comprising treating a subject in need thereof by daily subcutaneous injection of SEQ ID NO. 2 resulting in a Cmax plasma level of SEQ ID NO. 2 between 255.57 pg/mL and 364.3 pg/mL, a plasma $T_{max}$ for SEQ ID NO. 2 of between 0.251 hours and 1.01 hours, a plasma $t_{1/2}$ for SEQ ID NO. 2 of between 1.585 hours and 3.015 hours and a net plasma $AUC_{(0\text{-}inf)}$ of SEQ ID NO. 2 between 311.54 pg h/mL and 874.34 pg h/mL.

In some embodiments this invention provides a method of treatment of osteoporosis comprising treating a subject in need thereof by daily subcutaneous injection of 80 µg SEQ ID NO. 2 resulting in a Cmax plasma level between 255.57 pg/mL and 364.3 pg/mL, a plasma $T_{max}$ for SEQ ID NO. 2 between 0.251 hours and 1.01 hours, a plasma $t_{1/2}$ for SEQ ID NO. 2 of between 1.585 hours and 3.015 hours and a net plasma $AUC_{(0\text{-}inf)}$ of SEQ ID NO. 2 between 541.99 pg h/mL and 1569.21 pg h/mL.

In some embodiments this invention provides a method of treatment of osteoporosis comprising treating a subject in need thereof by daily subcutaneous injection of SEQ ID NO. 2 resulting in a plasma Cmax level between 89.8 pg/mL and 128.2 pg/mL of SEQ ID NO. 2, a plasma $T_{max}$ for SEQ ID NO. 2 between 0.250 hours and 3.05 hours, a plasma $t_{1/2}$ for SEQ ID NO. 2 of between 0.806 hours and 1.294 hours and a net plasma $AUC_{(0\text{-}3.00h)}$ of SEQ ID NO. 2 between 89.549 pg h/mL and 253.611 pg h/mL.

In some embodiments this invention provides a method of treatment of osteoporosis comprising treating a subject in need thereof by daily subcutaneous injection of 20 µg SEQ ID NO. 2 resulting in a plasma Cmax level between 89.8 pg/mL and 128.2 pg/mL of SEQ ID NO. 2 and a plasma $T_{max}$ for SEQ ID NO. 2 between 0.250 hours and 3.05 hours and a plasma $t_{1/2}$ for SEQ ID NO. 2 of between 0.806 hours and 1.294 hours and a net plasma $AUC_{(0\text{-}3.00h)}$ of SEQ ID NO. 2 between 89.549 pg h/mL and 253.611 pg h/mL.

In some embodiments this invention provides a method of treatment of osteoporosis comprising treating a subject in need thereof by daily subcutaneous injection of SEQ ID NO. 2 resulting in a plasma Cmax level of SEQ ID NO. 2 between 129.3 pg/mL and 284.4 pg/mL, a plasma $T_{max}$ for SEQ ID NO. 2 for SEQ ID NO. 2 between 0.349 hours and 1.00 hours, a plasma $t_{1/2}$ for SEQ ID NO. 2 of between 1.033 hours and 1.827 hours and a net plasma $AUC_{(0\text{-}3.49h)}$ of SEQ ID NO. 2 between 188.28 pg h/mL and 627.68 pg h/mL.

In some embodiments this invention provides a method of treatment of osteoporosis comprising treating a subject in need thereof by daily subcutaneous injection of 40 µg SEQ ID NO. 2 resulting in a plasma Cmax level of SEQ ID NO. 2 between 129.3 pg/mL and 284.4 pg/mL, a plasma $T_{max}$ for SEQ ID NO. 2 between 0.349 hours and 1.00 hours, a plasma $t_{1/2}$ for SEQ ID NO. 2 of between 1.033 hours and 1.827 hours and a net plasma $AUC_{(0\text{-}3.49h)}$ of SEQ ID NO. 2 between 188.28 pg h/mL and 627.681 pg h/mL.

In some embodiments this invention provides a method of treatment of osteoporosis comprising treating a subject in need thereof by daily subcutaneous injection of SEQ ID NO. 2 resulting in a Cmax plasma level of SEQ ID NO. 2 between 367.2 pg/mL and 504.8 pg/mL, a plasma $T_{max}$ for SEQ ID NO. 2 of between 0.500 hours and 1.00 hours, a plasma $t_{1/2}$ for SEQ ID NO. 2 of between 1.265 hours and 2.115 hours and a net plasma $AUC_{(0\text{-}6.00h)}$ of SEQ ID NO. 2 between 619.55 pg h/mL and 1386.45 pg h/mL.

In some embodiments this invention provides a method of treatment of osteoporosis comprising treating a subject in need thereof by daily subcutaneous injection of 80 µg SEQ ID NO. 2 resulting in a Cmax plasma level between 367.2 pg/mL and 504.8 pg/mL, a plasma $T_{max}$ for SEQ ID NO. 2 between 0.500 hours and 1.00 hours, a plasma $t_{1/2}$ for SEQ ID NO. 2 of between 1.265 hours and 2.115 hours and a net plasma $AUC_{(0\text{-}6.00h)}$ of SEQ ID NO. 2 between 619.55 pg h/mL and 1386.45 pg h/mL.

For purposes of this invention, Cmax refers to the maximum concentration that is measured in the plasma. $T_{max}$ is the time at which the maximum concentration occurs. AUC refers to the integral area under the curve for a given time interval. $AUC_{(0\text{-}inf)}$ refers to the area under the curve as extrapolated out to infinity or (maximum area under the curve). $AUC_{(0\text{-}t)}$ refers to the area under the curve at the time in hours listed. For example, $AUC_{(0\text{-}7h)}$ indicates the area under the curve after 7 hours. $t_{1/2}$ refers to the ½ life of the drug.

For the purposes of this disclosure, the therapeutic utility of these compounds includes "treating" a human and methods of treatment or treating a subject, human or patient, where treating is understood to include treating, preventing, or ameliorating the symptoms associated with, or reducing the incidence of, reducing the pathogenesis of, facilitating the recovery from or delaying the onset of the syndrome, illness, malady or condition being considered. As it pertains to osteoporosis and the methods of this invention, a method of treatment should also be understood to include a method of preventing osteoporosis. Increasing bone mineral density in a population with osteoporosis can accordingly be deemed a treatment for osteoporosis in that patient population. Likewise, preventing osteoporosis can be accomplished by administering the compositions and compounds of this invention to a patient population that does not yet have osteoporosis. In some embodiments of this invention, the patient population being administered the compositions and/or according to the methods of this invention are at increased risk for osteoporosis or who already have osteoporosis. It should also be appreciated that osteopenia is included with osteoporosis for purposes of this invention.

One of skill in the art appreciates that the several disorders are associated with osteoporosis and so it should be appreciated that the methods and compositions of this invention are useful for treating osteoporosis from the many origins and risk factors from which osteoporosis and osteopenia arise including but not limited to osteogenesis imperfecta, Mafan syndrome, hemochromatosis, hypophosphatasia, glycogen storage diseases, homocysinuria, Ehlers-Danlos syndrome, porhyria, Menke's syndrome, epidermolysis bullosa and Gaucher's disease.

A pharmaceutically acceptable salt is a salt which is suitable for administration to a subject, such as, a human. The peptides of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like. The peptides of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

The compositions of the present invention typically do not show any or show reduced side-effects such as hypercalcemia and typically do not increase the stimulation of bone resorption at the dosage listed above. This reduction in side effects allows for administration of higher doses than commercially available osteoporosis drugs.

The compositions of the present invention can be administered by injection as described herein or by pulmonary or transdermal delivery.

The compositions of the present invention may be administered alone or in combination with an additional therapeutic agent, such as an antiresorptive therapy, for example, bisphosphonates and calcitonin.

EXEMPLIFICATION

Example 1

Demonstrates Glu$^{22,25}$, Leu$^{23,28,31}$, Aib$^{29}$, Lys$^{26,30}$]hPTHrP(1-34)NH$_2$ (SEQ ID NO.: 2) Stability at Low Acetate Concentration (1 mM), without Stabilizer

TABLE 1

| Material | Supplier | Unitary Formula (per cartridge) |
|---|---|---|
| (SEQ ID NO.: 2) | Ipsen Ireland | 0.140 mg (free base) |
| Tri-hydrate sodium acetate 0.1 N | Prolabo | 14.6 mg 1 |
| Acetic acid 0.1 N | Prolabo | .9 mg qs pH 5.1 |
| Water for Injection | Meram | qs 1.4 g |
| Type I clear glass Cartridge 1.5 ml, washed, siliconised and sterilised | Bünderglass via Vetter | 1 |

TABLE 1-continued

| Material | Supplier | Unitary Formula (per cartridge) |
|---|---|---|
| Grey PTFE bromobutyl cartridge rubber stopper | Daïkyo | 1 |
| Chlorobutyl rubber-metal cartridge crimp | West Pharmaceutical | 1 | qs = quantity sufficient to achieve

The formulation delivered 100 mcg of (SEQ ID NO.: 2) per 0.1 ml. (SEQ ID NO.: 2) was dissolved in Water for Injection containing dilute acetate buffer to give pH 5.1 was used.

Results confirm excellent chemical stability over 24 months, at 5° C. as shown in FIG. 1. This solution contains no stabilizer or preservative and only 6 mM acetate buffer.

In summation for (SEQ ID NO.: 2), stabilizer is not needed to give good stability in solution.

Example 2

Use of Citric Acid Buffer in Lyophilised Form of (SEQ ID NO.: 2)

TABLE 2

| Material | Supplier | Unitary Formula (per vial) |
|---|---|---|
| (SEQ ID NO.: 2) | Ipsen Ireland | 0.1 mg (free base) |
| Dextran 70 | Interchemical | 50 mg |
| Citric acid 0.25% (w/v) | Prolabo | qs pH 4.5* |
| Water for injections** | Meram | qs 1 g |
| Type I clear glass vial, 11-13 ml | Verretubex | 1 |
| Grey chlorobutyl PTFE stopper, 20 mm | Daïkyo | 1 |
| Flip-off metal crimp | West Pharma | 1 |

**to get pH 5-5.5 after lyophilisation removed after freeze-drying step.

The solutions in Table 2 were reconstituted with NaCl 0.9%, to give:

ONE vial of 2 ml (=50 μg/ml) providing 10 to 80 μg/d doses (with injections of 200 μl to 1.6 ml), or ONE vial of 5 ml (=20 μg/ml solution) providing 5 to 40 μg/d doses (with injections of 250 μl-2 ml).

Citric acid was used to adjust pH and Dextran was used to provide a bulking agent to aid cake formation during lyophilization.

Figure 2:
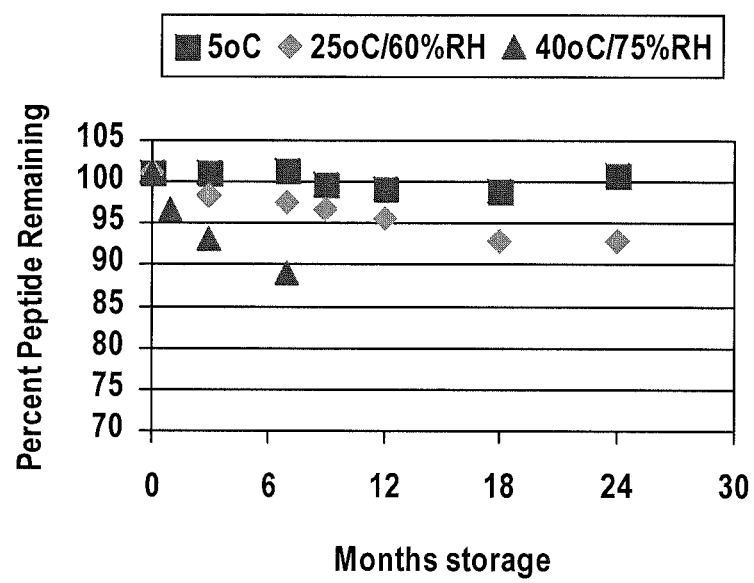
FIG. 2 is a graph showing the stability of lyophilized SEQ ID NO. 2 over 24 months at 5° C. 25° C. and 40° C.
Figure 3:
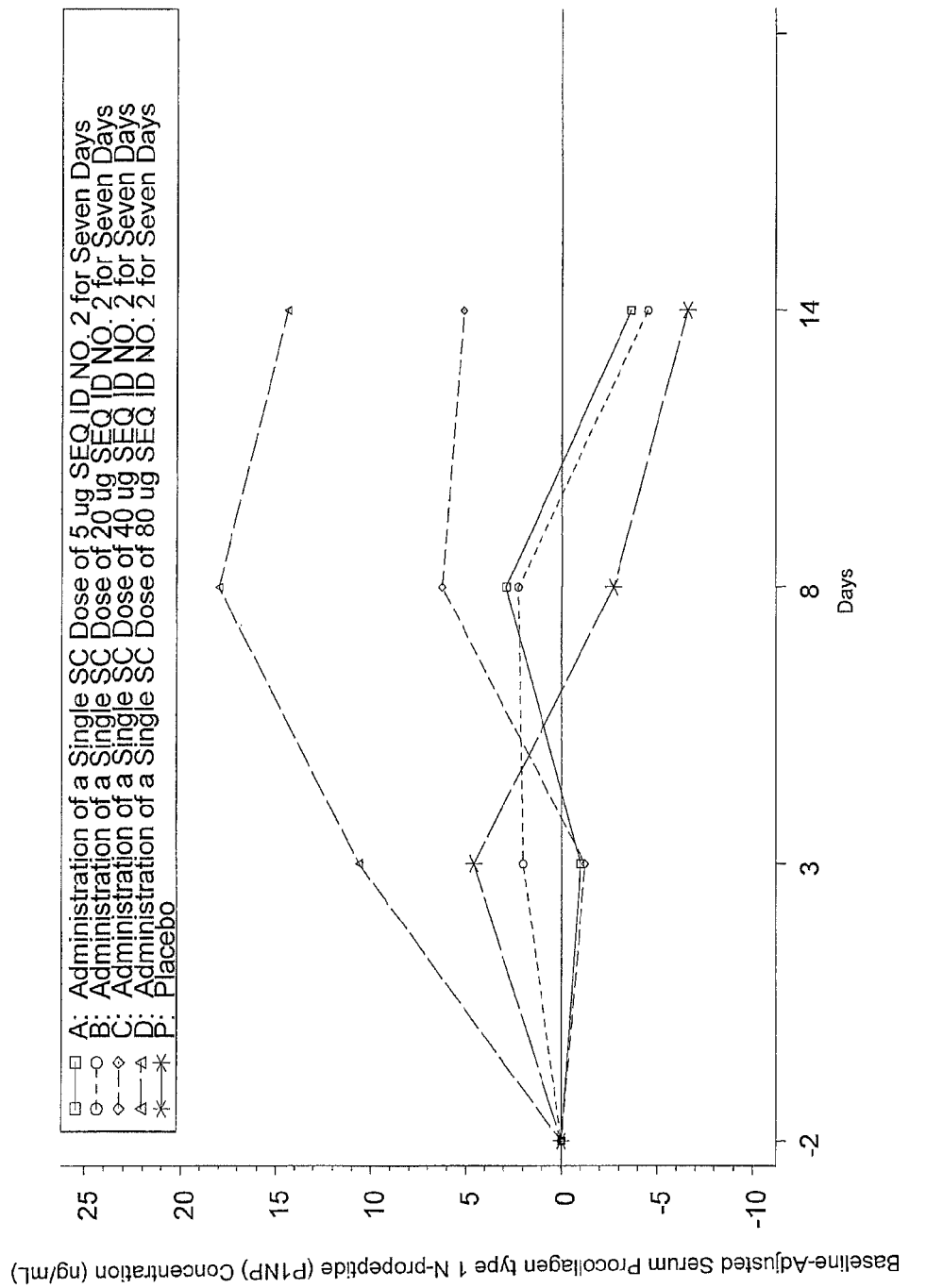
FIG. 3 is a graph showing the plasma levels of the bone formation marker Procollagen type 1 N-propeptide (P1NP) (ng/mL) through two days pre-dosing, seven days of dosing and seven days post-dosing. A=5 μg SEQ ID NO. 2; B=20 μg SEQ ID NO. 2; C=40 μg SEQ ID NO.2; D=80 μg SEQ ID NO.2; P=Placebo.
Figure 4:
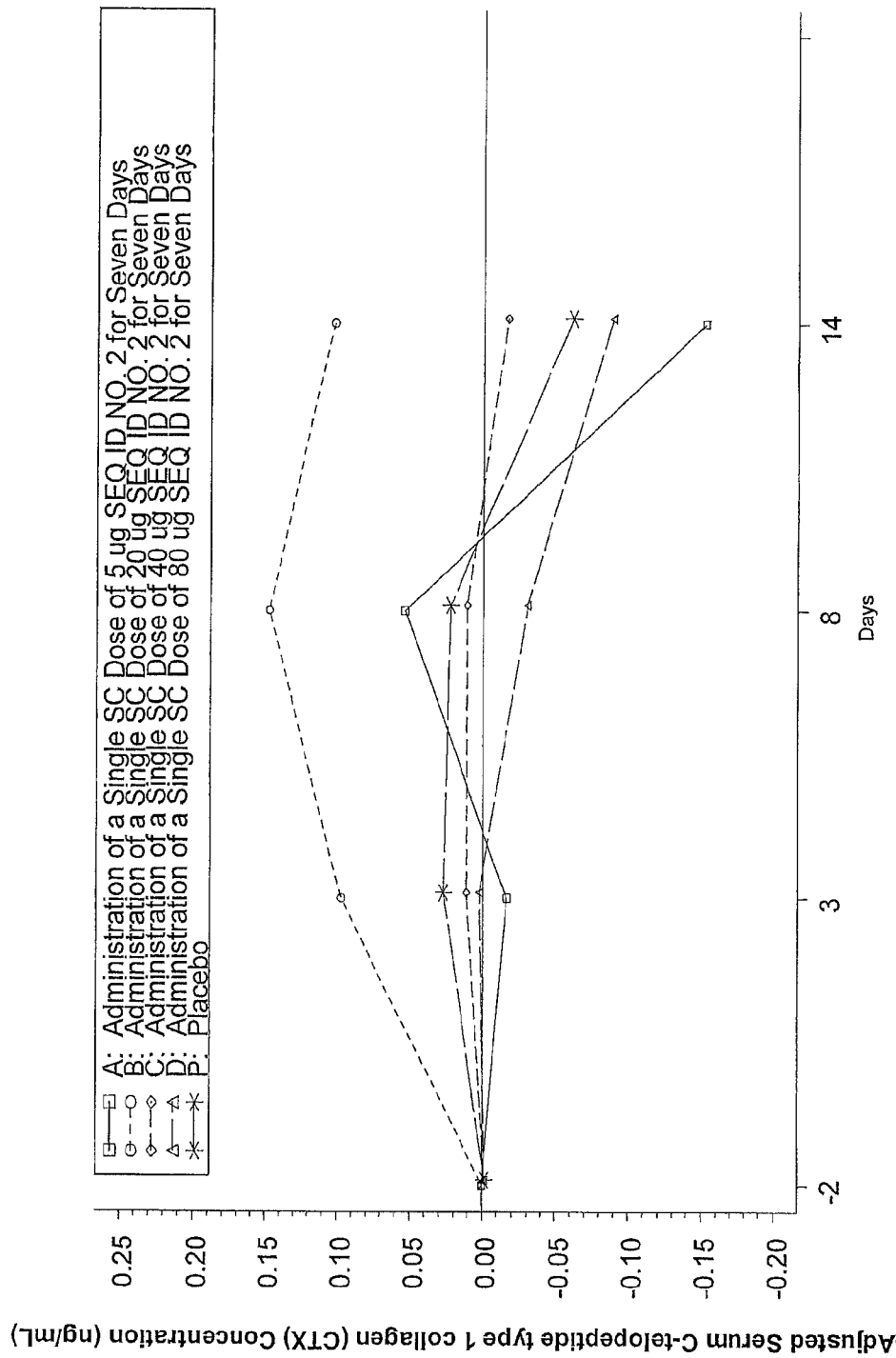
FIG. 4 is a graph showing the plasma levels of the bone resorption marker Serum C-telopeptide type-1 collagen (Ctx) (ng/mL) through two days pre-dosing, seven days dosing and seven days post-dosing. A=5 μg SEQ ID NO. 2; B=20 μg SEQ ID NO. 2; C=40 μg SEQ ID NO.2; D=80 μg SEQ ID NO.2; P=Placebo.
Figure 5:
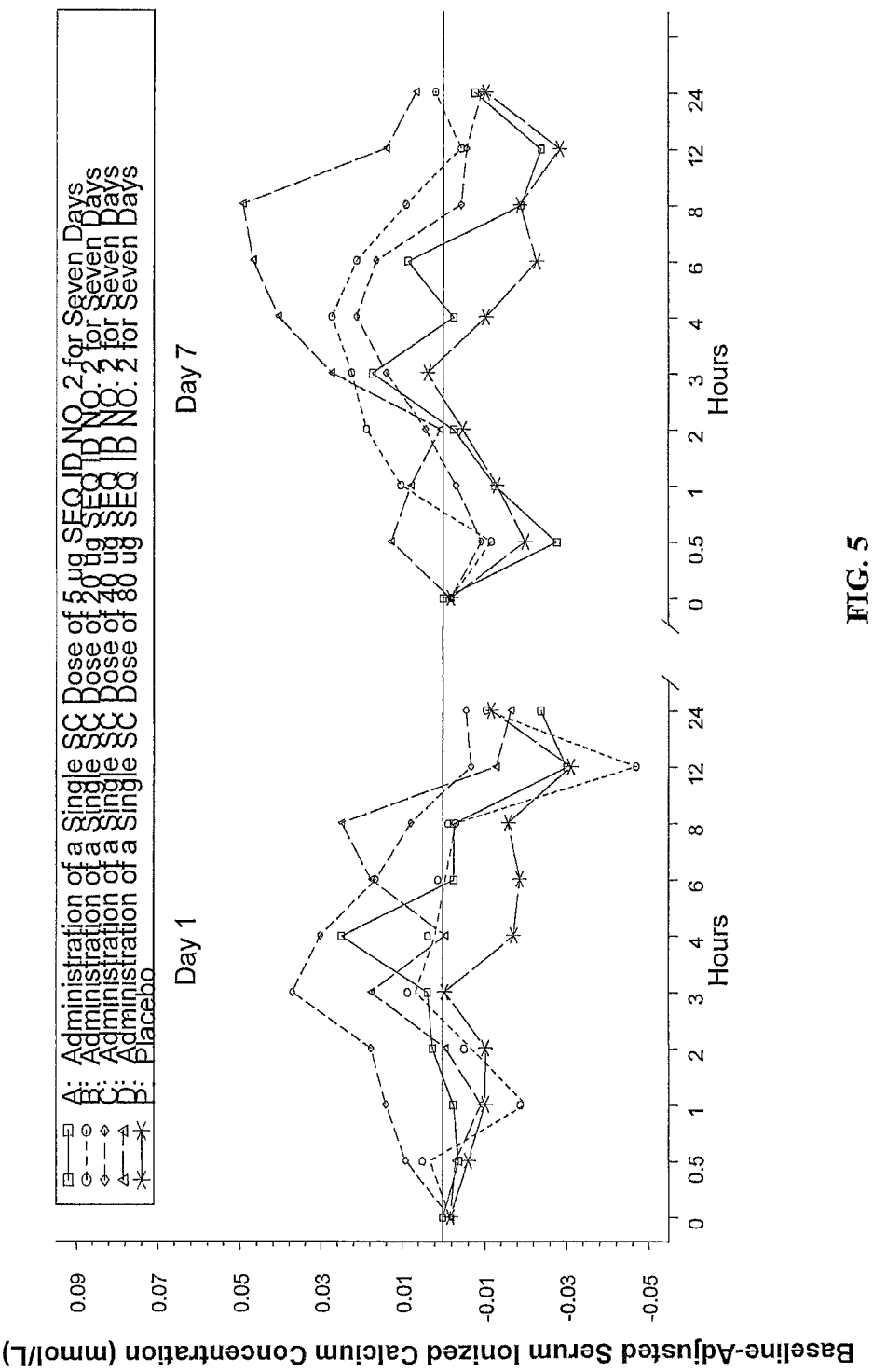
FIG. 5 is a graph showing the plasma levels of serum ionized calcium (mmol/L) through 24 hours post-first dose and 24 hours post-seventh dose. A=5 μg SEQ ID NO. 2; B=20 μg SEQ ID NO. 2; C=40 μg SEQ ID NO.2; D=80 μg SEQ ID NO.2; P=Placebo.
Figure 6:
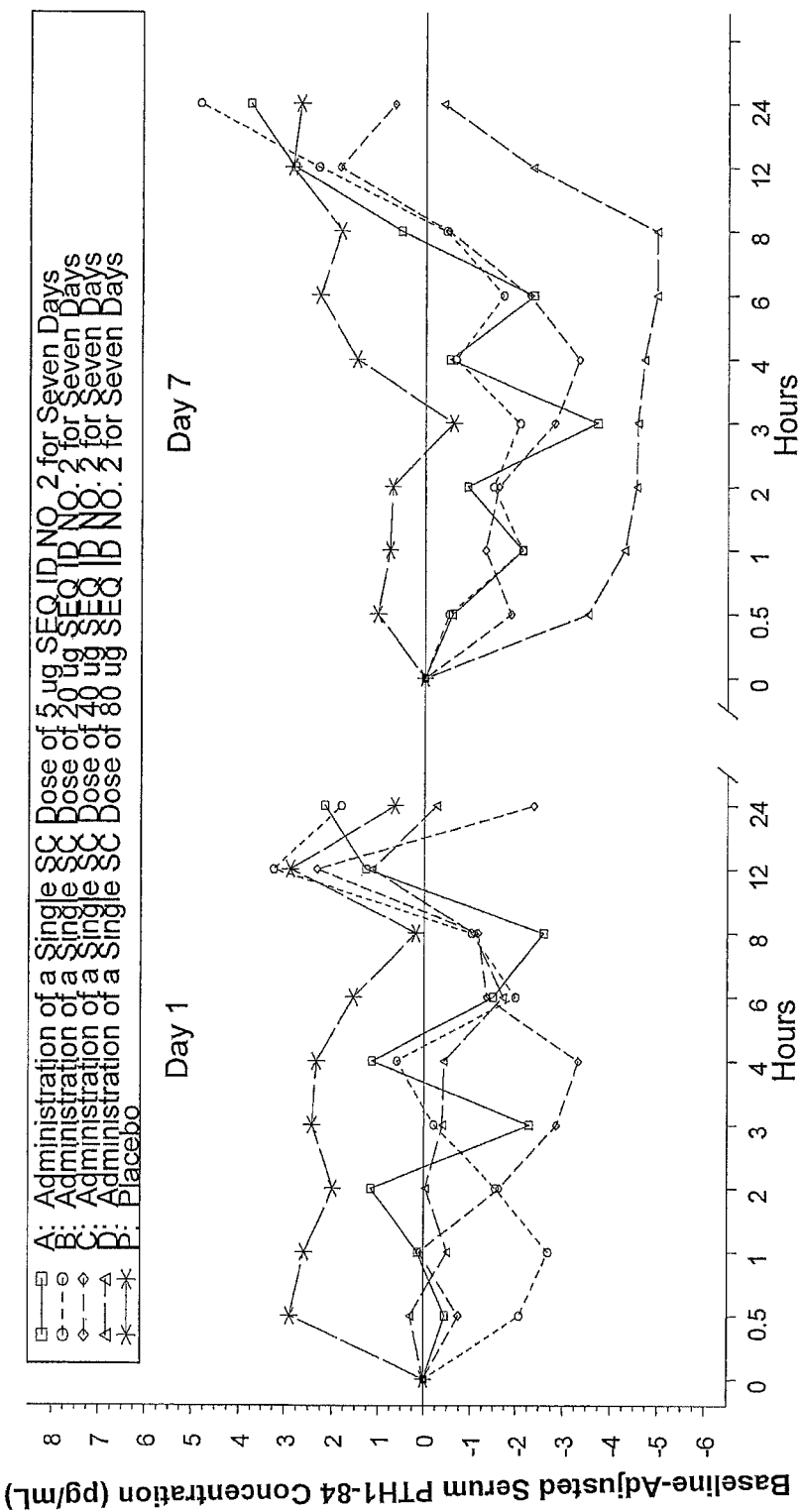
FIG. 6 is a graph showing the plasma levels of PTH (pG/mL) through 24 hours post-first dose and 24 hours post-seventh day dose. A=5 μg SEQ ID NO. 2; B=20 μg SEQ ID NO. 2; C=40 μg SEQ ID NO.2; D=80 μg SEQ ID NO.2; P=Placebo.

The solutions described were lyophilized in glass vials, and stored at various temperatures for up to 24 months. The content of Glu$^{22,25}$, Leu$^{23,28,31}$, Aib$^{29}$, Lys$^{26,30}$]hPTHrP(1-34)NH$_2$ (SEQ ID NO.: 2), purity and physical tests were conducted on samples removed from storage at different times. Results are presented in FIG. 2, for peptide concentration, as percent remaining. The data in FIG. 2 shows excellent stability over 24 months at 2-8° C.

Example 3

Screening of Formulations for Glu$^{22,25}$, Leu$^{23,28,31}$, Aib$^{29}$, Lys$^{26,30}$]hPTHrP(1-34)NH$_2$ (SEQ ID NO.: 2) to Compare Different Preservatives TABLE 3 below shows Methyparaben and Benzyl Alcohol are not suitable preservatives for use with Glu$^{22,25}$, Leu$^{23,28,31}$, Aib$^{29}$, Lys$^{26,30}$]hPTHrP(1-34)NH$_2$ (SEQ ID NO.: 2), as precipitation and/or inactivity in preservative activity was seen.

TABLE 3

|  | Example 3a | Example 3b | Example 3c | Example 3d | Example 3e |
|---|---|---|---|---|---|
| Methylparaben | 1.5 mg/mL | 1.35 mg/mL | — | — | — |
| Propylparaben | — | 0.15 mg/mL | — | — | — |
| Phenol | — | — | 5 mg/mL | — | — |
| Chlorocresol | — | — | — | 3 mg/mL | — |
| Benzyl alcohol | — | — | — | — | 10 mg/mL |
| Preservative effectiveness test | Failed | Pass | Pass | Pass | Pass |
| Observation or Issues | Precipitation observed | — | — | — | — |
| Preservative effectiveness test after storage 4.5 months at 5° C. | Not Tested as precipitated initially | Pass | Pass | Pass | Fail |

Solutions were prepared containing [Glu$^{22,25}$, Leu$^{23,28,31}$, Aib$^{29}$, Lys$^{26,30}$]hPTHrP(1-34)NH$_2$ (SEQ ID NO.: 2) 2 mg/ml, acetate buffer 6 mM and water for injection, with various different preservatives added at concentrations recommended for effective antimicrobial activity. Solutions were prepared at room temperature, by dissolution of the various ingredients in water for injection, with stirring over <30 minutes to ensure complete dissolution, Solutions were filtered through 0.2 micron filter and filled into glass vials, to which a rubber stopper was applied and crimped in place to ensure complete closure.

The solution with methylparaben was unacceptable due to precipitation and inactivity immediately after manufacture of the solution. The solutions were then stored for up to 3 months at 25° C., and up to 4.5 months at 5° C. and the preservative effectiveness test repeated. as described in Example 5.

Example 4

Evaluation of Anti-microbial Preservative Effectiveness of Various Concentrations of [Glu$^{22,25}$, Leu$^{23,28,31}$, Aib$^{29}$, Lys$^{26,30}$]hPTHrP(1-34)NH$_2$ (SEQ ID NO.: 2) Compositions (Stability Study)

TABLE 4

|  | P87228 | P87229 | P87230 | P87231 |
|---|---|---|---|---|
| (SEQ ID NO.: 2) | 2 mg/mL | 2 mg/mL | 2 mg/mL | 2 mg/mL |
| Anti-microbial | Phenol 5 mg/mL | Chloro-cresol 3 mg/mL | Chloro-cresol 2 mg/mL | Benzyl alcohol 10 mg/mL |
| Acetate buffer | pH 5.1 | pH 5.1 | pH 5.1 | pH 5.1 |

The solutions were tested according to European Pharmacopoeia, Chapter 5.1.3 "Efficacité de la conservation anti-microbienne" (Anti-microbial effectiveness test) to prove the effectiveness of the preservative.

TABLE 5

| | Preservative effectiveness test after manufacturing | | | | | |
|---|---|---|---|---|---|---|
| | Initial | | Nb of cfu present/preparation (plate-count method) | | | |
| Organisms: Bacteria | organism concentration in cfu/mL | Test interval | P87228 Phenol 5 mg/ml | P87229 Chlorocresol 3 mg/ml | P87230 Chlorocresol 2 mg/ml | P87231 Benzyl alc. 10 mg/ml |
| Staphylococcus aureus | 3.8 × 10$^5$ | T 0 | 3.4 × 10$^5$ | <5 | <5 | 4.7 × 10$^5$ |
| | | T + 6 hrs | <5 | <5 | <5 | 6.8 × 10$^2$ |
| | | T + 24 hrs | <5 | <5 | <5 | <5 |
| | | T + 28 days | 5 (*) | <5 | <5 | <5 |
| Pseudomonas aeruginosa | 1.3 × 10$^6$ | T 0 | 5 | <5 | <5 | 1.5 × 10$^2$ |
| | | T + 6 hrs | <5 | <5 | <5 | <5 |
| | | T + 24 hrs | <5 | <5 | <5 | <5 |
| | | T + 28 days | <5 | <5 | <5 | <5 |
| E. coli | 6.7 × 10$^5$ | T 0 | 7.2 × 10$^3$ | <5 | <5 | 1.1 × 10$^5$ |
| | | T + 6 hrs | <5 | <5 | <5 | <5 |
| | | T + 24 hrs | <5 | <5 | <5 | <5 |
| | | T + 28 days | <5 | <5 | <5 | <5 |
| | Initial | | Nb of cfu present/preparation (plate-count method) | | | |
| Organism: Yeast and mold | organism concentration in cfu/mL | Test interval | P87228 Phenol 5 mg/ml | P87229 chlorocresol 3 mg/ml | P87230 chlorocresol 2 mg/ml | P87231 Benzyl alc. 10 mg/ml |
| Aspergillus niger | 3.4 × 10$^5$ | T 0 | 4.0 × 10$^5$ | <5 | <5 | 4.1 × 10$^5$ |
| | | T + 7 days | <5 | <5 | <5 | <5 |
| | | T + 28 days | <5 | <5 | <5 | <5 |

TABLE 5-continued

| | | | | | | |
|---|---|---|---|---|---|---|
| Candida albicans | $3.9 \times 10^5$ | T 0 | $4.4 \times 10^5$ | <5 | <5 | $3.8 \times 10^5$ |
| | | T + 7 days | <5 | <5 | <5 | 5 |
| | | T + 28 days | <5 | <5 | <5 | <5 |
| Results: | Conform | — | Conform | Conform | Conform | Conform |

Preservative effectiveness test results after 3 months storage at 25° C.

| | Initial | | Nb of cfu present/preparation (plate-count method) | | | |
|---|---|---|---|---|---|---|
| Organisms: Bacteria | organism concentration in cfu/mL | Test interval (days) | P87228 Phenol 5 mg/ml | P87229 chlorocresol 3 mg/ml | P87230 chlorocresol 2 mg/ml | P87231 Benzyl alc. 10 mg/ml |
| Staphylococcus aureus | $2.7 \times 10^5$ (P87228, P87229, P87231) | 0 hr | $1.9 \times 10^5$ | <5 | <5 | $3.8 \times 10^5$ |
| | | 6 hr | 30 | <5 | <5 | $5.9 \times 10^3$ |
| | | 24 hr | <5 | <5 | <5 | <5 |
| | $5.2 \times 10^5$ (P87230) | 28 day | <5 | <5 | <5 | <5 |
| Pseudomonas aeruginosa | $9.9 \times 10^5$ (P87228, P87229, P87231) | 0 hr | <5 | <5 | <5 | <5 |
| | | 6 hr | <5 | <5 | <5 | <5 |
| | | 24 hr | <5 | <5 | <5 | <5 |
| | $8.5 \times 10^5$ (P87230) | 28 day | <5 | <5 | <5 | <5 |
| E. coli | $6.8 \times 10^5$ (P87228, P87229, P87231) | 0 hr | $1.7 \times 10^5$ | <5 | <5 | $8.0 \times 10^4$ |
| | | 6 hr | <5 | <5 | <5 | 5 |
| | | 24 hr | <5 | <5 | <5 | <5 |
| | $9.5 \times 10^5$ (P87230) | 28 day | <5 | <5 | <5 | <5 |

| | Initial | | Nb of cfu present/preparation (plate-count method) | | | |
|---|---|---|---|---|---|---|
| Organism: Yeast and mold | organism concentration in cfu/mL | Test interval | P87228 Phenol 5 mg/ml | P87229 Chlorocresol 3 mg/ml | P87230 Chlorocresol 2 mg/ml | P87231 Benzyl alc. 10 mg/ml |
| Aspergillus niger | $3.3 \times 10^5$ (P87228, P87229, P87231) | 0 hr | $3.8 \times 10^5$ | 55 | 70 | $4.1 \times 10^5$ |
| | | 7 day | <5 | <5 | <5 | <5 |
| | | 28 day | <5 | <5 | <5 | <5 |
| | $4.1 \times 10^5$ (P87230) | | | | | |
| Candida albicans | $2.7 \times 10^5$ (P87228, P87229, P87231) | 0 hr | $4.0 \times 10^5$ | <5 | <5 | $3.8 \times 10^5$ |
| | | 7 day | <5 | <5 | <5 | <5 |
| | | 28 day | <5 | <5 | <5 | <5 |
| | $3.7 \times 10^5$ (P87230) | | | | | |
| Results: | Conform | — | Conform | Conform | Conform | Not Conform |

Preservative effectiveness test results after 4.5 months storage at 5° C.

| | Initial | | Nb of cfu present/preparation (plate-count method) | | | |
|---|---|---|---|---|---|---|
| Organisms: Bacteria | organism concentration in cfu/mL | Test interval (days) | P87228 Phenol 5 mg/ml | P87229 Chlorocresol 3 mg/ml | P87230 Chlorocresol 2 mg/ml | P87231 Benzyl alc. 10 mg/ml |
| Staphylococcus aureus | $5.4 \times 10^5$ | 0 hr | $4.1 \times 10^5$ | <5 | <5 | $5.1 \times 10^5$ |
| | | 6 hr | <5 | <5 | <5 | $7.2 \times 10^3$ |
| | | 24 hr | <5 | <5 | <5 | <5 |
| | | 28 day | <5 | <5 | <5 | <5 |
| Pseudomonas aeruginosa | $9.7 \times 10^5$ | 0 hr | <5 | <5 | <5 | <5 |
| | | 6 hr | <5 | <5 | <5 | <5 |
| | | 24 hr | <5 | <5 | <5 | <5 |
| | | 28 day | <5 | <5 | <5 | <5 |
| E. coli | $6.1 \times 10^5$ | 0 hr | $7.0 \times 10^4$ | 5 | 5 | $4.2 \times 10^4$ |
| | | 6 hr | <5 | <5 | <5 | <5 |
| | | 24 hr | <5 | <5 | <5 | <5 |

TABLE 5-continued

| | | | Nb of cfu present/preparation (plate-count method) | | | |
|---|---|---|---|---|---|---|
| | Initial | | | | | |
| Organism: Yeast and mold | organism concentration in cfu/mL | Test interval | P87228 Phenol 5 mg/ml | P87229 Chlorocresol 3 mg/ml | P87230 Chlorocresol 2 mg/ml | P87231 Benzyl alc. 10 mg/ml |
| | | 28 day | <5 | <5 | <5 | <5 |
| *Aspergillus niger* | $5.3 \times 10^5$ | 0 hr | $3.7 \times 10^5$ | $1.8 \times 10^3$ | $7.5 \times 10^3$ | $4.1 \times 10^5$ |
| | | 7 day | <5 | <5 | <5 | <5 |
| | | 28 day | <5 | <5 | <5 | <5 |
| *Candida albicans* | $4.1 \times 10^5$ | 0 hr | $4.5 \times 10^5$ | <5 | 5 | $4.5 \times 10^5$ |
| | | 7 day | <5 | <5 | <5 | <5 |
| | | 28 day | <5 | <5 | <5 | <5 |
| Results: | Conform | — | Conform | Conform | Conform | Not Conform |

(*) *Bacillus* Gram +, different from *St. Aureus* –> result conform
Nb of cfu = number of colony forming units TABLE 5 shows Phenol, Chlorocresol and Benzyl Alcohol all produce compliant results immediately after manufacture for both Bacteria and Yeasts/moulds. After 3 and 4.5 months storage, the preservative efficacy is maintained for Phenol and Chlorocresol, for both Bacteria and Yeasts/moulds. However, for Benzyl Alcohol, the efficacy against Bacteria is not compliant, as the data shows insufficient rate of kill against *S Aureus* (TABLE 5).

Example 5

Chemical Stability of Different Formulations

Table 6 details the chemical stability of the formulations described in Example 4.

TABLE 6

$\text{Glu}^{22,25}, \text{Leu}^{23,28,31}, \text{Aib}^{29}, \text{Lys}^{26,30}$ ]hPTHrP(1-34)NH$_2$ (SEQ ID NO.: 2) stability results

| | | Storage conditions: 25° C., 60% RH (SEQ ID NO.: 2) content in mg/mL (% initial concentration at t = 0) | | |
|---|---|---|---|---|
| Batch | Composition | 0 month | 1 month | 3 months |
| P87228 | (SEQ ID NO.: 2) (2 mg/ml)/ Phenol (5 mg/ml) | 1.90 (100%) | 1.88 (98.9%) | 1.83 (96.3%) |
| P87229 | (SEQ ID NO.: 2) (2 mg/ml)/ Chlorocresol (3 mg/ml) | 1.98 (100%) | 1.96 (99.0%) | 1.94 (98.0%) |
| P87231 | (SEQ ID NO.: 2) (2 mg/ml)/ Benzyl Alcohol (10 mg/ml) | 1.93 (100%) | 1.89 (97.9%) | 1.86 (96.4%) |

| | | Storage conditions: 5° C. (SEQ ID NO.: 2) content in mg/mL (% initial concentration at t = 0) | | |
|---|---|---|---|---|
| Batch | Composition | 0 month | 3 month | 4.5 month |
| P87228 | (SEQ ID NO.: 2) (2 mg/ml)/ Phenol (5 mg/ml) | 1.90 (100%) | 1.91 (100.5%) | 1.89 (99.5%) |
| P87229 | (SEQ ID NO.: 2) (2 mg/ml)/ Chlorocresol (3 mg/ml) | 1.98 (100%) | 1.96 (99.0%) | 1.97 (99.5%) |
| P87231 | (SEQ ID NO.: 2) (2 mg/ml)/ Benzyl Alcohol (10 mg/ml) | 1.93 (100%) | 1.94 (100.5%) | 1.92 (99.5%) |

As can be seen from TABLE 6 and $\text{Glu}^{22,25}, \text{Leu}^{23,28,31}, \text{Aib}^{29}, \text{Lys}^{26,30}$ ]hPTHrP(1-34)NH$_2$(SEQ ID NO.: 2) solution stability is not significantly influenced by the preservative selected. TABLE 7 details the content of each preservative for the same formulations.

TABLE 7

Preservative stability results

| | | Storage conditions : 25° C., 60% RH Preservative content in mg/ml (% initial concentration at t = 0) | | |
|---|---|---|---|---|
| Batch | Composition | 0 month | 1 month | 3 month |
| P87228 | (SEQ ID NO.: 2) (2 mg/ml)/ Phenol (5 mg/ml) | 4.86 (100%) | 4.82 (99.2%) | 4.79 (98.6%) |
| P87229 | (SEQ ID NO.: 2) (2 mg/ml)/ Chlorocresol (3 mg/ml) | 2.78 (100%) | 2.70 (97.1%) | 2.56 (92.1%) |
| P87231 | (SEQ ID NO.: 2) (2 mg/ml)/ Benzyl Alcohol (10 mg/ml) | 9.92 (100%) | 9.83 (99.1%) | 9.82 (99.0%) |

| | | Storage conditions : 5° C. Preservative content in mg/mL (% initial concentration at t = 0) | | |
|---|---|---|---|---|
| Batch | Composition | 0 month | 3 month | 4.5 month |
| P87228 | (SEQ ID NO.: 2) (2 mg/ml)/ Phenol (5 mg/ml) | 4.86 (100%) | 4.83 (99.4%) | 4.84 (99.6%) |
| P87229 | (SEQ ID NO.: 2) (2 mg/ml)/ Chlorocresol (3 mg/ml) | 2.78 (100%) | 2.73 (98.2%) | 2.74 (98.6%) |
| P87231 | (SEQ ID NO.: 2) (2 mg/ml)/ Benzyl Alcohol (10 mg/ml) | 9.92 (100%) | 9.89 (99.7%) | 9.94 (100.2%) |

As can be seen from TABLE 7 chlorocresol is the preservative which has the lower stability, with greater loss in preservative content under both 5 and 25° C. storage.

Example 6

Clinical Study of Subjects Treated with $\text{Glu}^{22,25}, \text{Leu}^{23,28,31}, \text{Aib}^{29}, \text{Lys}^{26,30}$ ]hPTHrP(1-34)NH$_2$ (SEQ ID NO.: 2)

A randomized, double-blind, placebo-controlled, multiple-dose design study of $\text{Glu}^{22,25}, \text{Leu}^{23,28,31}, \text{Aib}^{29}, \text{Lys}^{26,30}$ ]hPTHrP(1-34)NH$_2$ (SEQ ID NO.: 2) was conducted at 2 sites. A total of 39 eligible subjects were sequentially enrolled into 1 of 4 study groups consisting of 10 subjects each, with the exception of Group 2, which had 9 subjects. Within each study group, 8 subjects were randomly assigned to receive SEQ ID NO.: 2 and 2 subjects were randomly assigned to receive placebo (In Group 2 only, 1 subject received placebo). All subjects in the study were judged by the investigator to be healthy, normal volunteers. The test products were $\text{Glu}^{22,25}, \text{Leu}^{23,28,31}, \text{Aib}^{29}, \text{Lys}^{26,30}$ ]hPTHrP(1-34)NH$_2$ (SEQ ID NO.: 2) (0.1 mg/vial) and Placebo (0.9% sodium chloride injection, USP). All subjects received a single subcutaneous (SC) dose of Glu[22,25], Leu[23,28,31], Aib[29], Lys[26,30]]hPTHrP(1-34)NH$_2$ (SEQ ID NO.: 2) or placebo for 7 days. The dosages and number of subjects per study group and overall are shown below in TABLE 8.

TABLE 8

| Study Group | Dose | Days of Dosing | Number of Subjects Randomized | | |
|---|---|---|---|---|---|
| | | | Total Number of Subjects | SEQ ID NO.: 2 | Placebo |
| 1 | 5 μg | 7 | 10 | 8 | 2 |
| 2 | 20 μg | 7 | 9 | 8 | 1 |
| 3 | 40 μg | 7 | 10 | 8 | 2 |
| 4 | 80 μg | 7 | 10 | 8 | 2 |
| | | Total | 39 | 32 | 7 |

Criteria for Evaluation:

Pharmacokinetics: PK sampling for plasma SEQ ID NO.: 2 on Days 1 and 7 was performed at the following time points: Predose (0 hour), 0.25, 0.5, 1, 1.5, 2, 3, 4, 6, 8, 12, and 24 hours postdose. Additionally, predose samples were taken for trough drug analysis on Days 3 to 6. The following PK parameters were computed for Days 1, and 7: AUC$_{(0-t)}$, AUC$_{(0-\infty)}$ (Day 1 only), AUC$_{(0-\tau)}$, AUCR (Day 1 only), C$_{max}$, T$_{max}$, T$_{last}$, CL/F, Kel, t$_{1/2}$, and AI (Day 7 only). These parameters were calculated from the overall (24 hours) plasma concentration-versus-time profiles by noncompartmental methods using WinNonhin® Pro Version 5.01 and SAS® Version 8.2. Moreover, the ln-transformed PK parameters C$_{max}$, AUC$_{(0-t)}$, AUC$_{(0-\tau)}$, and AUC$_{(0-\infty)}$ are presented.

Pharmacodynamics

Serum PD samples (total and ionized calcium, phosphorus, PTH[1-84], Procollagen type 1 N-propeptide [P1NP], C-telopeptide type 1 collagen [CTX], and 1,25-dihydroxyvitamin D [vitamin D]) were obtained at the following time points: Serum PD Samplings were Performed at the Following Time Points:

Total Calcium and Phosphorus:
 Predose Days: Days −30 and −2
 Days 1 and 7: Predose (0 hour), 0.5, 1, 2, 3, 4, 6, 8, 12, and 24 hours postdose
 Days 3, 4, 5, 6, and 14
Ionized Calcium:
 Predose (Day −30)[1]
 Days 1 and 7: Predose (0 hour), 0.5, 1, 2, 3, 4, 6, 8, 12, and 24 hours postdose

[1] Deleted for Groups 2, 3, and 4 per Amendment 3 to the protocol.

PTH(1-84) and 1,25-Dihydroxyvitamin D (Vitamin D):
 Days 1 and 7: Predose (0 hour), 0.5, 1, 2, 3, 4, 6, 8, 12, and 24 hours postdose Procollagen Type 1 N-Propeptide (P1NP) and C-Telopeptide Type 1 Collagen (CTX):
 Predose (Day −2), Days 3, 8, and 14.

Urine PD Samples (Calcium, Phosphorus, Cyclic AMP [c-AMP], and Creatinine) were Obtained at the Following Time Points:
 Day −1/Day 1: −24 to −18 hours, −18 to −12 hours, and −12 hours to 0 hours. Days 1 and 7: 0 to 6 hours, 6 to 12 hours, and 12 to 24 hours.

The following parameters in urine were presented for each of the PD markers using SAS® Version 8.2: Volume (Vol.), concentration (Conc.), amount (Ae), cumulative amount (Cum. Ae), and excretion rates.

Statistical Methods:

Pharmacokinetics:

Plasma concentration and PK parameters for SEQ ID NO.: 2 were listed by subject and summarized by treatment and day using descriptive statistics (mean, standard deviation [SD], coefficient of variation [CV %], standard error of the mean [SEM], sample size [N], minimum [min], maximum [max], and median). Additionally, geometric means and ln-transformed values were provided for C$_{max}$ and AUCs.

Dose proportionality was evaluated for Days 1 and 7 SEQ ID NO.: 2 data using the following power model:

$$Ln(Y) = \beta_0 + \beta Ln\, Dose + \epsilon$$

where Y represents the PK parameters AUC$_{(0-\infty)}$, AUC$_{(0-\tau)}$, AUC$_{(0-t)}$, and C$_{max}$. Dose proportionality requires that β=1 for dose-dependent parameters.

The model was used to calculate the 95% confidence intervals (CI) for the slope of the ln-transformed PK parameters AUCs and C$_{max}$. Dose proportionally was concluded if the 95% CI for the PK parameters included the value of 1.

For those cases in which dose proportionality could not be concluded within all doses investigated, dose proportionality analysis was performed for the first 3 (by excluding the highest dose) and the last 3 doses (by excluding the lowest dose).

Pharmacokinetic/Pharmacodynamic Analysis:

The plots of plasma SEQ ID NO.: 2 and calcium concentrations did not indicate a clear relationship between SEQ ID NO.: 2 and calcium concentrations; therefore, no PK/PD modeling work was performed for this study.

Pharmacodynamics:

The data for each PD marker in serum (total and ionized calcium, phosphorus, PTH(1-84), 1,25-dihydroxyvitamin D, P1NP, and CTX) and in urine (calcium, phosphorus, c-AMP, and creatinine) following SEQ ID NO.: 2 and placebo doses were listed for each subject and summarized by SEQ ID NO.: 2 dose using descriptive statistics (mean, SD, CV %, SEM, N, min, max, and median).

Pharmacokinetic Results:

The arithmetic mean and the SD of plasma SEQ ID NO.: 2 PK parameters following subcutaneous (SC) administration of SEQ ID NO.: 2 doses for Days 1 and 7 are presented Table 9 and Table 10.

TABLE 9

Summary of Plasma SEQ ID NO.: 2 Pharmacokinetic Parameters
Following 5 μg Through 80 μg SEQ ID NO.: 2 Doses-Day 1

| Pharmacokinetic Parameters | Treatment A Mean ± SD (N) | Treatment B Mean ± SD (N) | Treatment C Mean ± SD (N) | Treatment D Mean ± SD (N) |
|---|---|---|---|---|
| C$_{max}$ (pg/mL) | 43.1 ± 10.7 (7) | 115 ± 53.9 (8) | 223 ± 99.0 (8) | 310 ± 54.3 (8) |
| T$_{max}$ (hr)# | 0.566 (0.531, 1.00) (7) | 0.296 (0.250, 0.624) (8) | 0.494 (0.262, 0.579) (8) | 0.752 (0.251, 1.01) (8) |

TABLE 9-continued

Summary of Plasma SEQ ID NO.: 2 Pharmacokinetic Parameters
Following 5 µg Through 80 µg SEQ ID NO.: 2 Doses-Day 1

| Pharmacokinetic Parameters | Treatment A Mean ± SD (N) | Treatment B Mean ± SD (N) | Treatment C Mean ± SD (N) | Treatment D Mean ± SD (N) |
|---|---|---|---|---|
| $T_{last}$ (hr)# | 2.01 (1.50, 4.00) (7) | 2.01 (1.00, 4.00) (8) | 4.00 (1.51, 6.01) (8) | 7.00 (4.00, 12.0) (8) |
| $AUC_{0-t}$ (pg*hr/mL) | 78.439 ± 45.472 (7) | 160.52 ± 110.83 (8) | 419.89 ± 275.15 (8) | 949.89 ± 493.58 (8) |
| $AUC_{0-inf}$ (pg*hr/mL) | 187.36 ± 54.536 (4) | 257.17 ± 119.05 (5) | 592.94 ± 281.40 (6) | 1055.6 ± 513.61 (8) |
| $AUC_{0-tau}$ (pg*hr/mL) | 186.92 ± 54.397 (4) | 257.16 ± 119.02 (5) | 592.90 ± 281.37 (6) | 1053.2 ± 511.27 (8) |
| $t_{1/2}$ (hr) | 2.59 ± 0.690 (4) | 1.05 ± 0.314 (5) | 1.65 ± 0.254 (6) | 2.30 ± 0.715 (8) |
| $K_{el}$ (1/hr) | 0.282 ± 0.0722 (4) | 0.713 ± 0.229 (5) | 0.428 ± 0.0603 (6) | 0.335 ± 0.127 (8) |
| AUCR | 0.521 ± 0.111 (4) | 0.828 ± 0.0449 (5) | 0.838 ± 0.0703 (6) | 0.892 ± 0.0369 (8) |
| CL/F (L/hr) | 28.56 ± 8.727 (4) | 94.20 ± 46.04 (5) | 84.15 ± 46.04 (6) | 94.61 ± 51.09 (8) |
| $\ln(C_{max})$ | 3.741 ± 0.2153 (7) | 4.643 ± 0.4890 (8) | 5.331 ± 0.4130 (8) | 5.722 ± 0.1732 (8) |
| $\ln(AUC_{0-t})$ | 4.241 ± 0.5166 (7) | 4.821 ± 0.8221 (8) | 5.844 ± 0.6783 (8) | 6.740 ± 0.5206 (8) |
| $\ln(AUC_{0-inf})$ | 5.200 ± 0.3016 (4) | 5.456 ± 0.4957 (5) | 6.280 ± 0.5203 (6) | 6.855 ± 0.5063 (8) |
| $\ln(AUC_{0-tau})$ | 5.198 ± 0.3007 (4) | 5.456 ± 0.4956 (5) | 6.280 ± 0.5202 (6) | 6.853 ± 0.5050 (8) |

= Tmax and Tlast are presented as Median (Minimum, Maximum)
Treatment A = Administration of a Single SC Dose of 5 µg SEQ ID NO.: 2 for Seven Days
Treatment B = Administration of a Single SC Dose of 20 µg SEQ ID NO.: 2 for Seven Days
Treatment C = Administration of a Single SC Dose of 40 µg SEQ ID NO.: 2 for seven Days
Treatment D = Administration of a Single SC Dose of 80 µg SEQ ID NO.: 2 for Seven Days

TABLE 10

Summary of Plasma SEQ ID NO.: 2 Pharmacokinetic Parameters
Following 5 µg Through 80 µg SEQ ID NO.: 2 Doses-Day 7

| Pharmacokinetic Parameters | Treatment A Mean ± SD (N) | Treatment B Mean ± SD (N) | Treatment C Mean ± SD (N) | Treatment D Mean ± SD (N) |
|---|---|---|---|---|
| $C_{max}$ (pg/mL) | 40.8 ± 7.63 (6) | 109 ± 19.2 (8) | 207 ± 77.7 (8) | 436 ± 68.8 (8) |
| $T_{max}$ (hr)# | 1.05 (0.514, 1.53) (6) | 0.512 (0.250, 3.05) (8) | 0.492 (0.349, 1.00) (8) | 0.507 (0.500, 1.00) (8) |
| $T_{last}$ (hr)# | 2.53 (1.50, 4.08) (6) | 3.00 (1.11, 4.00) (8) | 3.49 (2.00, 8.02) (8) | 6.00 (4.00, 8.02) (8) |
| $AUC_{0-t}$ (pg*hr/mL) | 80.704 ± 30.441 (6) | 171.58 ± 82.031 (8) | 407.98 ± 219.70 (8) | 1003.0 ± 383.45 (8) |
| $AUC_{0-tau}$ (pg*hr/mL) | . ± . (0) | 228.20 ± 95.154 (6) | 481.88 ± 226.19 (8) | 1080.3 ± 408.57 (8) |
| $t_{1/2}$ (hr) | . ± . (0) | 1.05 ± 0.244 (6) | 1.43 ± 0.397 (8) | 1.69 ± 0.425 (8) |
| $K_{el}$ (1/hr) | . ± . (0) | 0.694 ± 0.165 (6) | 0.527 ± 0.192 (8) | 0.437 ± 0.124 (8) |
| CL/F (L/hr) | . ± . (0) | 103.9 ± 53.01 (6) | 102.0 ± 53.34 (8) | 82.74 ± 26.95 (8) |
| AI | . ± . (0) | 1.10 ± 0.369 (5) | 0.844 ± 0.0673 (6) | 1.12 ± 0.353 (8) |
| $\ln(C_{max})$ | 3.694 ± 0.1912 (6) | 4.682 ± 0.1835 (8) | 5.266 ± 0.4068 (8) | 6.065 ± 0.1628 (8) |
| $\ln(AUC_{0-t})$ | 4.325 ± 0.4085 (6) | 5.039 ± 0.5086 (8) | 5.888 ± 0.5352 (8) | 6.851 ± 0.3623 (8) |
| $\ln(AUC_{0-tau})$ | . ± . (0) | 5.351 ± 0.4532 (6) | 6.078 ± 0.4879 (8) | 6.927 ± 0.3581 (8) |

= Tmax and Tlast are presented as Median (Minimum, Maximum)
Treatment A = Administration of a Single SC Dose of 5 µg SEQ ID NO.: 2 for Seven Days
Treatment B = Administration of a Single SC Dose of 20 µg SEQ ID NO.: 2 for Seven Days
Treatment C = Administration of a Single SC Dose of 40 µg SEQ ID NO.: 2 for Seven Days
Treatment D = Administration of a Single SC Dose of 80 µg SEQ ID NO.: 2 for Seven Days Overall, administration of increasing doses of SEQ ID NO.: 2 resulted in increasing rate and extent of exposure to SEQ ID NO.: 2. SEQ ID NO.: 2 was characterized by a rapid absorption following SC doses as mean $C_{max}$ was achieved within approximately 1 hour. Moreover, SEQ ID NO.: 2 had a short half-life with mean $t_{1/2}$ ranging from 1.05 hours to 2.59 hours. Apparent clearance was 28.56 L/hr following the lowest dose (5 μg) and ranged from 82.74 L/hr to 103.9 L/hr following the 20, 40, and 80 μg doses and, with the exception of the lowest dose remained fairly stable with increased doses of SEQ ID NO.: 2.

The results indicated that exposure to SEQ ID NO.: 2 was relatively comparable between Days 1 and 7 following SEQ ID NO.: 2 doses. Mean AI values ranged from 0.844 to 1.12, indicating that drug accumulation was negligible following multiple dosing of SEQ ID NO.: 2. Moreover, mean PK parameters values of $T_{max}$, $t_{1/2}$, and CL/F were comparable between Days 1 and 7.

The dose proportionality assessment of exposure to SEQ ID NO.: 2 in plasma resulting from SC doses of SEQ ID NO.: 2 is presented in the following table.

| Day | Pharmacokinetic Parameters | Slope | Standard Error | 95% CI |
|---|---|---|---|---|
| 1 | Cmax | 0.77861 | 0.1375 | (0.4935, 1.0637) |
|  | AUC(0 – t) | 0.90714 | 0.1237 | (0.6542, 1.1600) |
|  | AUC(0 – inf) | 0.99565 | 0.2024 | (0.5685, 1.4228) |
| 7 | Cmax | 0.99804 | 0.0985 | (0.7938, 1.2023) |
|  | AUC(0 – tau) | 1.14127 | 0.1649 | (0.7974, 1.4852) |

Dose Proportionality Analysis of Plasma SEQ ID NO.: 2 Following 5 μg Through 80 μg SEQ ID NO.: 2 Doses Dose proportionality was concluded if the CI for the ln-transformed parameters included the value of 1.
Dose proportionality for Cmax and AUC(0 – inf) was concluded following 20 μg, 40 μg, and 80 μg SEQ ID NO.: 2 doses.
Dose proportionality for AUC(0 – t) and AUC(0 – tau) was concluded following 5 μg, 20 μg, 40 μg, and 80 μg SEQ ID NO.: 2 doses.
Parameters were ln-transformed prior to analysis.

Pharmacodynamic Results:
Pharmacodynamic Markers in Serum:

Total calcium concentrations in serum remained within the reference range except for two subjects (placebo) and three subjects receiving the SEQ ID NO.: 2 doses. On Days 1 and 7, following SC administration of 5 to 80 μg SEQ ID NO.: 2 or placebo, mean total calcium levels marginally (±0.6 mg/dL) changed from predose levels. Total serum calcium concentrations following SEQ ID NO.: 2 doses mostly remained above the placebo level.

While in the first two doses, the majority of the ionized calcium measurements including baseline values were out of the reference range, in the second 2 doses, all the measurements were within the reference range.

The 95% CI of the slopes for ln-transformed PK parameters $C_{max}$, $AUC_{(0-t)}$, $AUC_{(0-\tau)}$, and $AUC_{(0-\infty)}$ indicated that, within the SEQ ID NO.: 2 dose range studied, the increases in PK parameters were dose-proportional (95% CI included the value of 1). While dose proportionality for $C_{max}$ and $AUC_{(0-\infty)}$ was concluded only following 20, 40, and 80 μg SEQ ID NO.: 2 doses, dose proportionality for $AUC_{(0-\tau)}$ and $AUC_{(0-t)}$ was concluded following all SEQ ID NO.: 2 doses investigated.

Mean baseline-adjusted ionized calcium levels slightly increased up to 0.04±0.02 mmol/L following 40 μg SEQ ID NO.: 2 dose on Day 1 and up to 0.05±0.02 mmol/L following 80 μg SEQ ID NO.: 2 dose on Day 7. Like total calcium, mean ionized calcium levels following SEQ ID NO.: 2 doses were generally higher than the mean values following placebo dose.

With the exception of 24 hours on Day 1, and 8 to 12 hours on Day 7, serum phosphorus concentrations following SEQ ID NO.: 2 and placebo doses remained below the predose levels on Days 1 and 7. Also, serum phosphorus concentrations following SEQ ID NO.: 2 doses were below the placebo concentration levels on both days.

Serum PTH (1-84) concentrations following SEQ ID NO.: 2 doses remained below the predose levels and placebo dose during most of the sampling times on both days. Serum PTH (1-84) concentrations following placebo dose consistently stayed above the baseline.

1,25-dihydroxyvitamin D concentrations in serum following SEQ ID NO.: 2 and placebo doses generally remained at predose levels on both Days 1 and 7, except following the 40 and 80 μg SEQ ID NO.: 2 doses which steadily rose above the predose levels after 2 hours postdose on Day 1 and most of the time on Day 7. Serum 1,25-dihydroxyvitamin D concentrations following SEQ ID NO.: 2 doses were mostly higher than placebo levels on both days.

P1NP concentrations in serum following SEQ ID NO.: 2 and placebo doses generally stayed near predose levels on Days 3, 8, and 14, except for 80 μg SEQ ID NO.: 2 dose which consistently stayed above baseline (maximum increase was up to 18±12 ng/mL) including Day 14. Mean P1NP serum levels following all doses of SEQ ID NO.: 2 showed some non-significant dose dependent elevation on Day 8. Mean serum CTX concentrations following SEQ ID NO.: 2 and placebo doses generally remained at or around the predose levels except following the 20 μg SEQ ID NO.: 2 dose where the concentrations consistently stayed above predose levels. The maximum increase at 0.15±0.18 ng/mL from baseline was within 1 SD.

Pharmacodynamic Markers in Urine:

On Day 1, mean urinary excretion rates of calcium following SEQ ID NO.: 2 doses and placebo subjects were approximately at predose levels. On Day 7, however, while mean urinary excretion rates of calcium following 40 and 80 μg SEQ ID NO.: 2 doses fluctuated at predose levels, those following the 5 and 20 μg SEQ ID NO.: 2 and placebo doses dropped below the predose levels.

Mean urinary excretion rates of phosphorus following SEQ ID NO.: 2 doses fluctuated around the predose levels. Mean phosphorus excretion rates following SEQ ID NO.: 2 doses on the last 2 intervals of Days 1 and 7 were lower than the first interval and at times fell below the predose levels.

Mean urinary excretion rates of c-AMP increased following SEQ ID NO.: 2 doses on both Days 1 and 7 but sharply dropped to predose and at times below the predose levels by the end of the sampling intervals.

Mean urinary excretion rates of creatinine following SEQ ID NO.: 2 and placebo doses fluctuated around the predose levels on Days 1 and 7.

While this invention has been particularly shown and described with references to example embodiments thereof, it will be understood by those skilled in the art that various changes in form and details may be made therein without departing from the scope of the invention encompassed by the appended claims.

What is claimed is:

1. A method of stimulating bone growth in a subject in need thereof comprising administering to said subject a storage stable composition comprising:
   a) a PTHrP having the sequence [Glu$^{22,25}$, Leu$^{23,28,31}$, Aib$^{29}$, Lys$^{26,30}$]hPTHrP(1-34)NH$_2$ (SEQ ID NO.: 2); and
   b) an effective amount of buffer to maintain the pH in a range of about 4.5 to about 5.6.

2. The method of claim 1, wherein said subject is administered the storage stable composition by subcutaneous injection of an amount of said composition containing from about 40 to about 45 μg of [Glu$^{22,25}$, Leu$^{23,28,31}$, Aib$^{29}$, Lys$^{26,30}$] hPTHrP(1-34)NH$_2$ (SEQ ID NO.2).

3. The method of claim 2, wherein said storage-stable composition further comprises phenol in a concentration from about 0.25 to about 5 mg/mL.

4. The method of claim 3, wherein said pH buffer is an acetate buffer.

5. The method of claim 1, wherein said subject is administered the storage stable composition by subcutaneous injection of an amount of said composition containing from about 75 to about 80 μg of [Glu$^{22,25}$, Leu$^{23,28,31}$, Aib$^{29}$, Lys$^{26,30}$] hPTHrP(1-34)NH$_2$ (SEQ ID NO.2).

6. The method of claim 5, wherein said storage-stable composition further comprises phenol in a concentration from about 0.25 to about 5 mg/mL.

7. The method of claim 6, wherein said pH buffer is an acetate buffer.

8. The method of claim 1, wherein said subject has a bone fracture.

9. The method of claim 2, wherein the subcutaneous injection is once per day, once every other day, twice per week, once per week, once every two weeks or once per month.

10. The method of claim 2, wherein the subcutaneous injection is single daily subcutaneous injection.

11. The method of claim 5, wherein the subcutaneous injection is once per day, once every other day, twice per week, once per week, once every two weeks or once per month.

12. The method of claim 5, wherein the subcutaneous injection is single daily subcutaneous injection.

* * * * *

SEQUENCE LISTING

```
<160> NUMBER OF SEQ ID NOS: 2

<210> SEQ ID NO 1
<211> LENGTH: 34
<212> TYPE: PRT
<213> ORGANISM: Homo Sapiens

<400> SEQUENCE: 1

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala

<210> SEQ ID NO 2
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 29
<223> OTHER INFORMATION: Aib
<220> FEATURE:
<221> NAME/KEY: AMIDATION
<222> LOCATION: 34

<400> SEQUENCE: 2

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Xaa Lys Leu His
            20                  25                  30

Thr Ala
```